(12) United States Patent
Mu et al.

(10) Patent No.: US 11,524,296 B2
(45) Date of Patent: Dec. 13, 2022

(54) CIRCULATING TUMOR CELL CAPTURE DEVICE, METHOD THEREOF AND METHOD FOR CIRCULATING TUMOR CELL CAPTURE AND DRUG SENSITIVITY ANALYSIS

(71) Applicants: NATIONAL TSING HUA UNIVERSITY, Hsinchu (TW); Taichung Veterans General Hospital, Taichung (TW)

(72) Inventors: Hsuan-Yo Mu, Hsinchu (TW); Jen-Huang Huang, Hsinchu (TW); Tzu-Hung Hsiao, Taichung (TW)

(73) Assignees: NATIONAL TSING HUA UNIVERSITY, Hsinchu (TW); TAICHUNG VETERANS GENERAL HOSPITAL, Taichung (TW)

( * ) Notice: Subject to any disclaimer, the term of this patent is extended or adjusted under 35 U.S.C. 154(b) by 560 days.

(21) Appl. No.: 16/777,363

(22) Filed: Jan. 30, 2020

(65) Prior Publication Data
US 2021/0053062 A1    Feb. 25, 2021

(30) Foreign Application Priority Data

Aug. 23, 2019 (TW) ................................ 108130311

(51) Int. Cl.
*B01L 3/00* (2006.01)
*C12Q 1/6886* (2018.01)

(52) U.S. Cl.
CPC ..... *B01L 3/502761* (2013.01); *B01L 3/50273* (2013.01); *C12Q 1/6886* (2013.01);
(Continued)

(58) Field of Classification Search
CPC ........... B01L 3/502761; B01L 3/50273; B01L 2200/0652; B01L 2200/027;
(Continued)

(56) References Cited

U.S. PATENT DOCUMENTS

2017/0128939 A1    5/2017    Abdolahad et al.

FOREIGN PATENT DOCUMENTS

| CN | 106754240 A | 5/2017 |
| WO | WO 2013/138522 A2 | 9/2013 |
| WO | WO 2019/010787 A1 | 1/2019 |

OTHER PUBLICATIONS

Walter et al. "A versatile lab-on-a-chip tool for modeling biological barriers" Sensors and Actuators B: Chemical. 222 (2016) 1209-1219. (Year: 2016).*

(Continued)

*Primary Examiner* — Michael L Hobbs
(74) *Attorney, Agent, or Firm* — Fay Sharpe LLP

(57) ABSTRACT

A circulating tumor cell capture device includes a chip system and a pump. The chip system includes a confluence chip and a lower chip set. The lower chip set is disposed at a lower surface of the confluence chip, and includes a channel chip, a split chip and a porous membrane. The channel chip is disposed at the lower surface of the confluence chip. The split chip is detachably stacked below the channel chip. The porous membrane is embedded in the channel chip. The specimen passes through the porous membrane and flow between the channel chip and the split chip to make the circulating tumor cell be captured by the porous membrane.

15 Claims, 24 Drawing Sheets
(3 of 24 Drawing Sheet(s) Filed in Color)

(52) U.S. Cl.
CPC .......... B01L 2200/0652 (2013.01); B01L 2300/0636 (2013.01); B01L 2300/0877 (2013.01)

(58) Field of Classification Search
CPC ..... B01L 2300/0636; B01L 2300/0877; C12Q 1/6886
See application file for complete search history.

(56) References Cited

OTHER PUBLICATIONS

Ramdane A. Harouaka et al., "Flexible Micro Spring Array Device for High-Throughput Enrichment of Viable Circulating Tumor Cells", Clinical Chemistry, published on Feb. 1, 2014, vol. 60, Issue 2, pp. 323-333, published by American Association for Clinical Chemistry, United States.

Aynur Abdulla et al., "High-Throughput Isolation of Circulating Tumor Cells Using Cascaded Inertial Focusing Microfluidic Channel", Analytical Chemistry, published on Mar. 14, 2018, vol. 90, Issue 7, pp. 4397-4405, published by American Chemical Society, United States.

Hsuan-Yo Mu et al., "Development of Live Circulating Tumor Cell Isolation and Analysis System for Multidrug Resistance Screening", 2019 International Advanced Drug Delivery Symposium & Annual Meeting of Biomaterials and Controlled Releases Society in Taiwan, dated on Mar. 28-29, 2019, Oral Presentation, Taiwan, R.O.C.

\* cited by examiner

CIRCULATING TUMOR CELL CAPTURE DEVICE, METHOD THEREOF AND METHOD FOR CIRCULATING TUMOR CELL CAPTURE AND DRUG SENSITIVITY ANALYSIS

RELATED APPLICATIONS

This application claims priority to Taiwan Application Serial Number 108130311, filed Aug. 23, 2019, which is herein incorporated by reference.

BACKGROUND

Technical Field

The present disclosure relates to a method of circulating tumor cell capture and a device thereof. More particularly, the present disclosure relates to a method of circulating tumor cell capture and a device thereof, which are for enriching captured circulating tumor cell and conducting a drug sensitivity analysis on the chip rapidly.

Description of Related Art

Circulating tumor cells (CTCs) are a kind of cancer cells arising in the circulatory system. The origin of circulating tumor cells is that, when a cancer tissue grows to a certain stage, the cancer tissue tends to grow on another organ or tissue. The cancer cells may grow into a new tumor when the cancer cells move to a certain organ or location through the circulatory system. This case is also called cancer metastasis.

In general, there are only 1-50 circulating tumor cells per 10 ml of blood in the circulatory system of a patient with cancer, but are $10^6$ leukocytes and $10^9$ red blood cells per 1 ml of blood, which leads to a pretty low ratio of circulating tumor cells in the blood. Therefore, the testing process of detecting circulating tumor cells is difficult, and cells in a specimen can only be separated through complicated pretreatments. To solve the difficulties faced today, there are different methods to enhance the effect of enriching circulating tumor cells.

The most widely used method of enriching circulating tumor cells nowadays is the FDA-cleared CellSearch® test. The CellSearch® test is based on a separating method of contacting to surface antigens, which is provided with high sensitivity (as circulating tumor cells can be captured by using only around 7.5 ml of whole blood). The capture method uses the difference that most circulating tumor cells have EpCAM expression which leukocytes that need to be separated do not have. Based on this difference, circulating tumor cells and other blood cells can be selected by using magnetic beads binding the antigens on surface. This method is often used to check cancer metastasis of a patient in clinical practice. Although the circulating tumor cells with particular antigens can be noticed by the immunoaffinity method and the quantity of the captured cells is measured by quantitating the antigens, it is possible to miss the circulating tumor cells without particular antigens, such as the circulating tumor cells in epithelial-mesenchymal transition (EMT) period, and lead to an underestimate of cancer screening of the patient. Moreover, in the process of capturing circulating tumor cells, the integrity of the circulating tumor cells is usually damaged due to the long binding time to the antibody, and due to the repeating washing and operating process. Chemical methods must be adopted to regain the circulating tumor cells from the magnetic beads, which destroys the few captured circulating tumor cells. Thus, living circulating tumor cells are hardly obtained by the immunoaffinity capture method. In this regard, it is still an unsolved problem to reach a good effect of enriching circulating tumor cells.

SUMMARY

According to one aspect of the present disclosure, a circulating tumor cell capture device is provided for capturing a circulating tumor cell in a specimen. The circulating tumor cell capture device includes a chip system and a pump. The chip system includes a confluence chip and a lower chip set. The confluence chip includes an upper surface and a lower surface, and the upper surface includes a specimen entrance, a specimen exit, a specimen entering channel and a specimen exiting channel. The specimen entrance communicates with the specimen entering channel, and the specimen exit communicates with the specimen exiting channel. The lower chip set is disposed at the lower surface of the confluence chip, and includes a channel chip, a split chip and a porous membrane. The channel chip is disposed at the lower surface of the confluence chip, and includes a channel chip upper layer and a channel chip lower layer. The channel chip upper layer includes one fluid access communicating with the specimen entering channel of the confluence chip, and an upper channel pattern structure. The channel chip lower layer is stacked below the channel chip upper layer. The channel chip lower layer includes another fluid access communicating with the fluid access of the channel chip upper layer, and a lower channel pattern structure corresponding to the upper channel pattern structure. The split chip is detachably stacked below the channel chip, and the split chip includes a split pattern channel for making the specimen split evenly. The porous membrane is disposed between the upper channel pattern structure and the lower channel pattern structure. The specimen is capable to pass through the porous membrane and flows between the channel chip and the split chip to make the circulating tumor cell be captured by the porous membrane. The pump is pipe-connected to the specimen exit and the specimen entrance of the confluence chip to make the specimen circularly flow in the chip system.

According to another aspect of the present disclosure, a method for circulating tumor cell capture includes steps as follows. A specimen is provided, the circulating tumor cell capture device of the aforementioned aspect is provided, a specimen pretreating step is performed and a capturing step is performed. The specimen pretreating step is to reduce an amount of blood cells in the specimen, in order to obtain a separated specimen with the circulating tumor cell. The capturing step is to draw the separated specimen into the specimen entrance, and make the separated specimen flow between the channel chip and the split chip and pass through the porous membrane by the pump, in order to make the circulating tumor cell be captured by the porous membrane.

According to still another aspect of the present disclosure, a method for circulating tumor cell capture and drug sensitivity analysis includes steps as follows. A specimen is provided, the circulating tumor cell capture device of the aforementioned aspect is provided, a specimen pretreating step is performed, a capturing step is performed, a detaching step is performed, a drug adding step is performed, a culturing step is performed and a drug sensitivity analysis result determining step is performed. The specimen pretreating step is to reduce an amount of blood cells in the specimen, in order to obtain a separated specimen with the circulating tumor cell. The capturing step is to draw the separated specimen into the specimen entrance, and make the separated specimen flow between the channel chip and the split chip and pass through the porous membrane by the pump, in order to make the circulating tumor cell be captured by the porous membrane. The detaching step is to detach the lower chip set from the chip system. The drug adding step is to detach the channel chip from the lower chip set, and to add at least one testing drug on the channel chip. The culturing step is to culture the channel chip with the at least one testing drug added under a culture condition for a culture time.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Circulating Tumor Cell Capture Device

Figure 1:
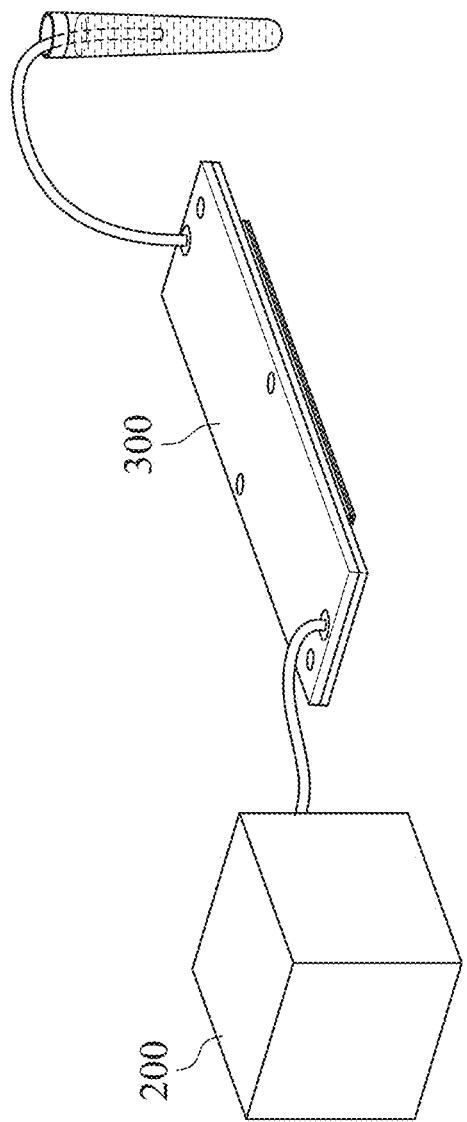
FIG. 1 is a schematic view according to one embodiment of a circulating tumor cell capture device of the present disclosure.
Figure 2:
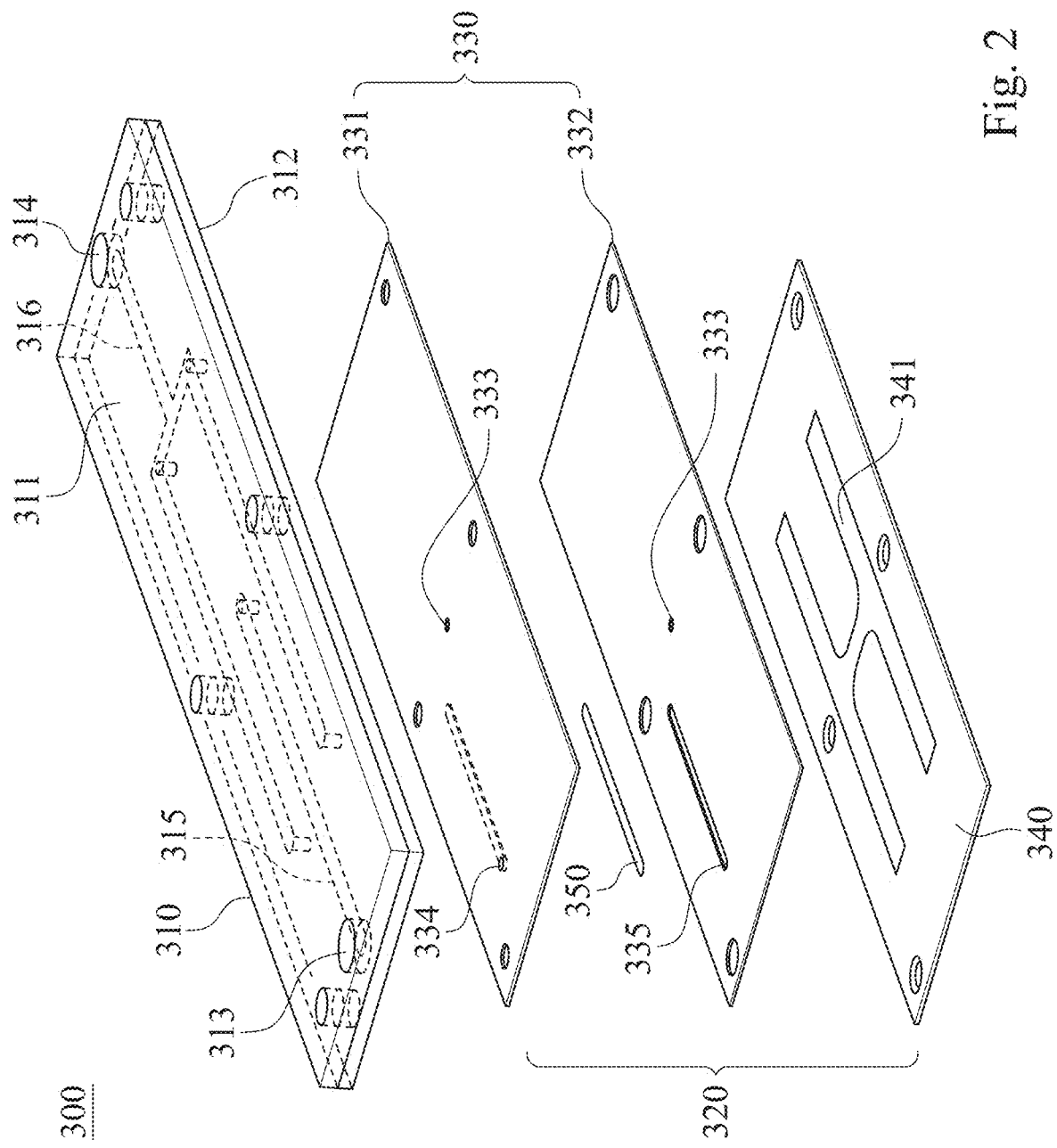
FIG. 2 is an exploded schematic view of a chip system according to one example of one embodiment of the circulating tumor cell capture device of FIG. 1.
Figure 3:
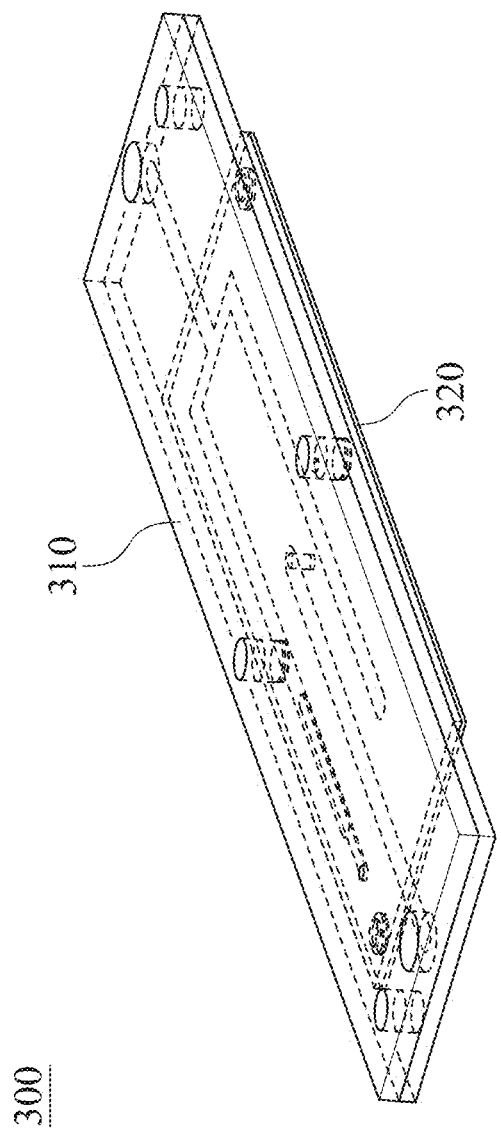
FIG. 3 is an assembly schematic view of the chip system according to one example of one embodiment of the circulating tumor cell capture device of FIG. 1.

Please refer to FIG. 1, FIG. 2 and FIG. 3. FIG. 1 is a schematic view according to one embodiment of a circulating tumor cell capture device 100 of the present disclosure. FIG. 2 is an exploded schematic view of a chip system 300 according to one example of one embodiment of the circulating tumor cell capture device 100 of FIG. 1. FIG. 3 is an assembly schematic view of the chip system 300 according to one example of one embodiment of the circulating tumor cell capture device 100 of FIG. 1. The circulating tumor cell capture device 100 includes a pump 200 and the chip system 300. The chip system 300 includes a confluence chip 310 and a lower chip set 320 sequentially from one side to another side.

The confluence chip 310 includes an upper surface 311 and a lower surface 312, and the upper surface 311 includes a specimen entrance 313, a specimen exit 314, a specimen entering channel 315 and a specimen exiting channel 316.

The specimen entrance 313 communicates with the specimen entering channel 315, and the specimen exit 314 communicates with the specimen exiting channel 316.

The lower chip set 320 is disposed at the lower surface 312 of the confluence chip 310, and includes a channel chip 330, a split chip 340 and a porous membrane 350.

The channel chip 330 is disposed at the lower surface 312 of the confluence chip 310, and includes a channel chip upper layer 331 and a channel chip lower layer 332. The channel chip upper layer 331 includes one fluid access 333 communicating with the specimen entering channel 315 of the confluence chip 310, and an upper channel pattern structure 334. The channel chip lower layer 332 is stacked below the channel chip upper layer 331. The channel chip lower layer 332 includes another fluid access 333 communicating with the fluid access 333 of the channel chip upper layer 331, and a lower channel pattern structure 335 corresponding to the upper channel pattern structure 334. Specifically, a number of the upper channel pattern structure 334 and the lower channel pattern structure 335 can be 1, respectively. When the channel chip upper layer 331 and the channel chip lower layer 332 are stacked together, the sizes and the positions of the upper channel pattern structure 334 and the lower channel pattern structure 335 are the same.

The split chip 340 is detachably stacked below the channel chip 330, and the split chip 340 includes a split pattern channel 341 for making the specimen split evenly. Specifically, the split pattern channel 341 of the split chip 340 can be an H-shaped channel for the specimen to split.

Specifically, the material of the confluence chip 310, the channel chip 330 and the split chip 340 of the chip system 300 can be, but not limited to, a plastic material such as polycarbonate (PC), polyethylene terephthalate (PET), polypropylene (PP) and acrylic.

The porous membrane 350 is disposed between the upper channel pattern structure 334 and the lower channel pattern structure 335. The specimen is able to pass through the porous membrane 350 and flow between the channel chip 330 and the split chip 340 to make the circulating tumor cell be captured by the porous membrane 350. Specifically, a pore diameter of the porous membrane 350 can be 5-12 micrometer to efficiently capture the circulating tumor cell. Specifically, the material of the porous membrane 350 can be, but not limited to, a material that is easily processed, such as polycarbonate, polyethylene terephthalate, polypropylene and poly(dimethylsiloxane) (PDMS).

The pump 200 is pipe-connected to the specimen exit 314 and the specimen entrance 313 of the confluence chip 310 to make the specimen circularly flow in the chip system 300. Specifically, the pump 200 can be a syringe pump which can pump the specimen in with a consistent flow rate and has a withdrawal function.

Figure 4A:
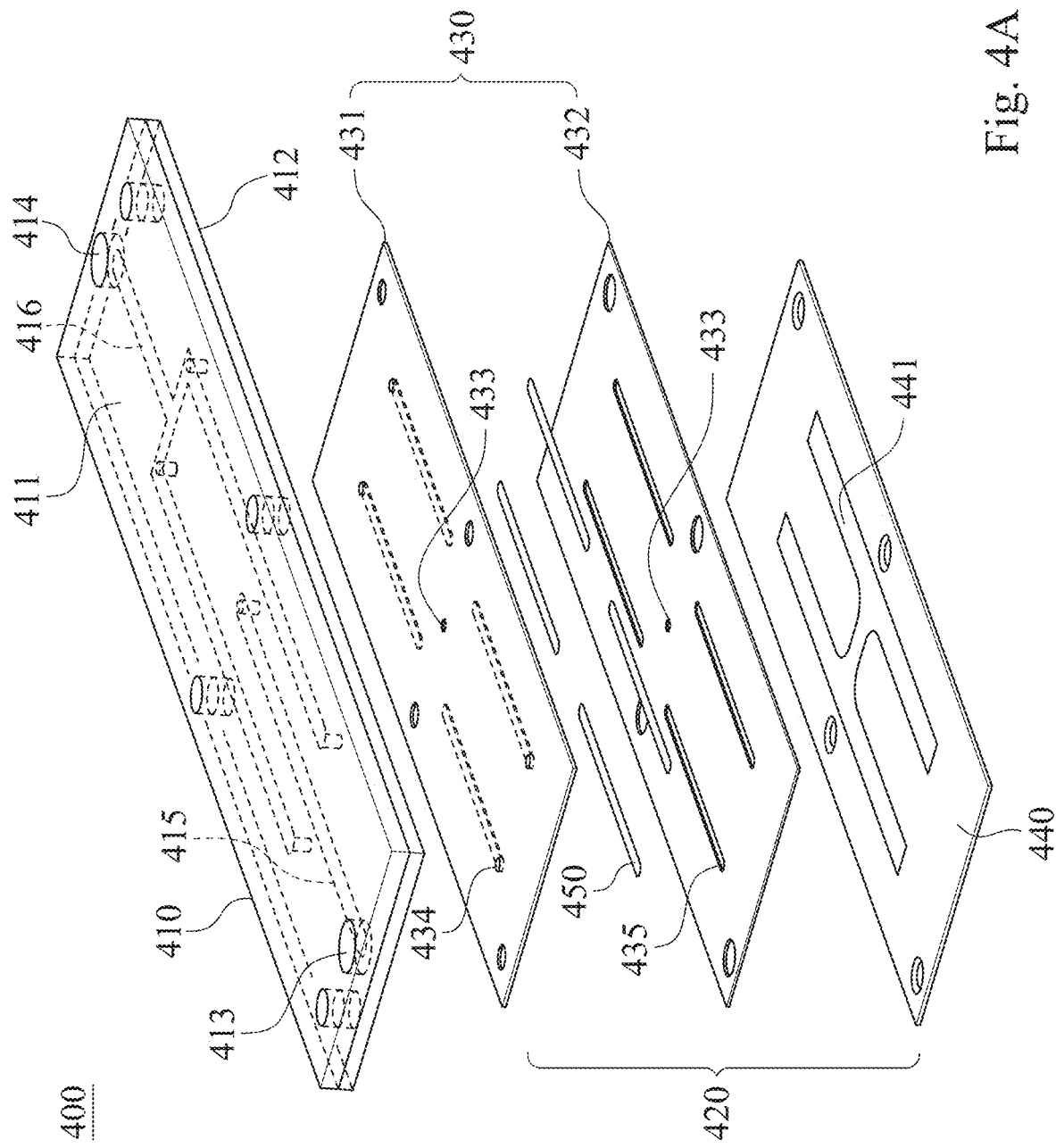
FIG. 4A is an exploded schematic view of a chip system according to another example of one embodiment of the circulating tumor cell capture device of FIG. 1.
Figure 4B:
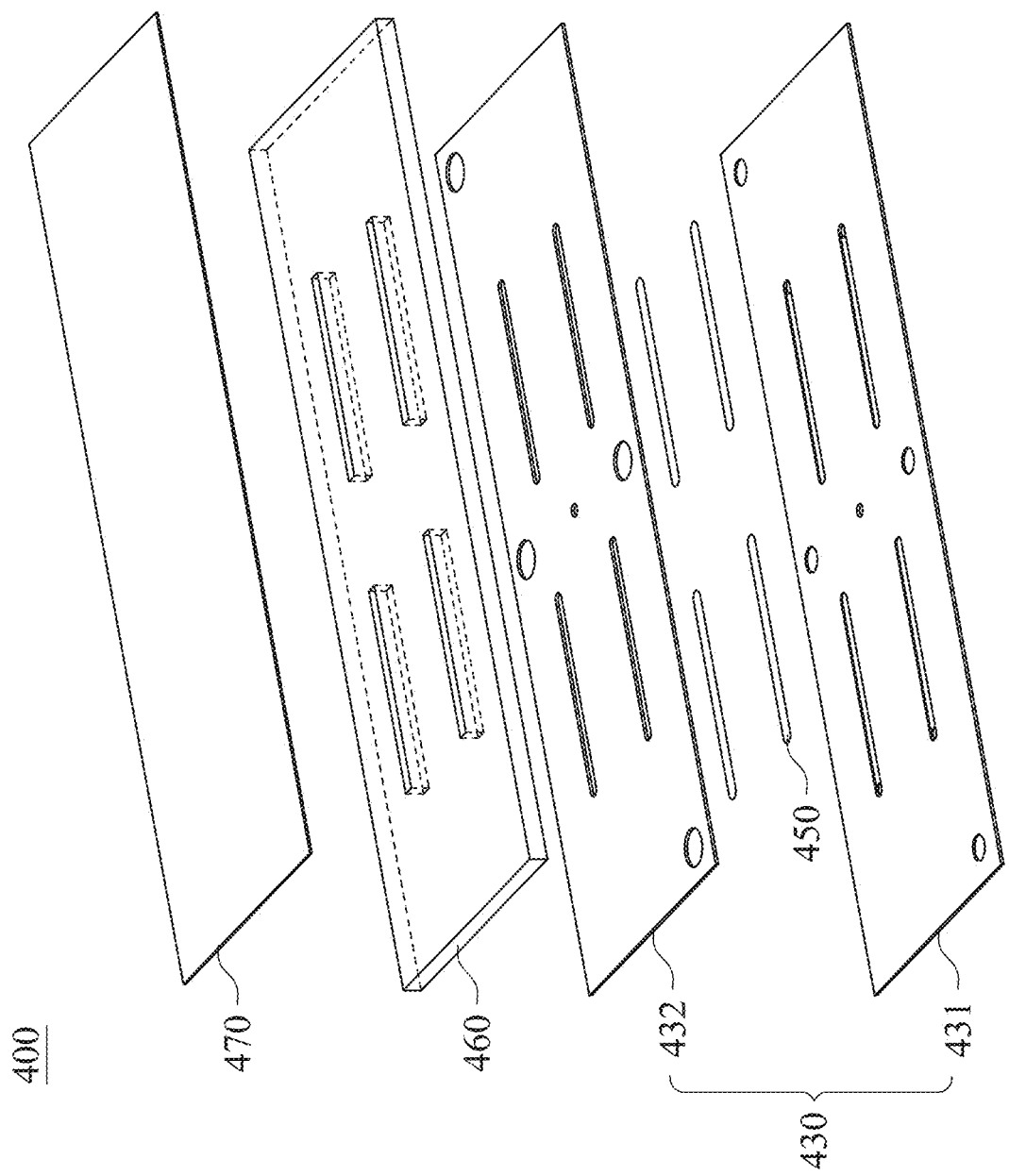
FIG. 4B is an exploded schematic view of a channel chip, a porous membrane, a first layer cover and a second layer cover of the chip system according to another example of one embodiment of the circulating tumor cell capture device of FIG. 1.

Please refer to FIG. 4A and FIG. 4B. FIG. 4A is an exploded schematic view of a chip system 400 according to another example of one embodiment of the circulating tumor cell capture device 100 of FIG. 1. FIG. 4B is an exploded schematic view of a channel chip 430, a porous membrane 450, a first layer cover 460 and a second layer cover 470 of the chip system 400 according to another example of one embodiment of the circulating tumor cell capture device 100 of FIG. 1.

The chip system 400 of FIG. 4A includes a confluence chip 410 and a lower chip set 420. The lower chip set 420 includes the channel chip 430, a split chip 440 and the porous membrane 450.

The confluence chip 410 includes an upper surface 411 and a lower surface 412, and the upper surface 411 includes a specimen entrance 413, a specimen exit 414, a specimen entering channel 415 and a specimen exiting channel 416. The specimen entrance 413 communicates with the specimen entering channel 415, and the specimen exit 414 communicates with the specimen exiting channel 416.

The channel chip 430 is disposed at the lower surface 412 of the confluence chip 410, and includes a channel chip upper layer 431 and a channel chip lower layer 432. The channel chip upper layer 431 includes one fluid access 433 communicating with the specimen entering channel 415 of the confluence chip 410, and an upper channel pattern structure 434. The channel chip lower layer 432 is stacked below the channel chip upper layer 431. The channel chip lower layer 432 includes another fluid access 433 communicating with the fluid access 433 of the channel chip upper layer 431, and a lower channel pattern structure 435 corresponding to the upper channel pattern structure 434. Specifically, a number of the upper channel pattern structure 434 and the lower channel pattern structure 435 can be 4, respectively. When the channel chip upper layer 431 and the channel chip lower layer 432 are stacked together, the sizes and the positions of the upper channel pattern structure 434 and the lower channel pattern structure 435 are the same. In this regard, at least one testing drug is able to be added on the channel chip 430 at the follow-up drug sensitivity analysis.

The split chip 440 is detachably stacked below the channel chip 430, and the split chip 440 includes a split pattern channel 441 for making the specimen split evenly. Specifically, the split pattern channel 441 of the split chip 440 can be an H-shaped channel for the specimen to split.

A number of the porous membrane 450 in the chip system 400 is 4, and the four porous membranes 450 are respectively disposed between the four upper channel pattern structures 434 and the four lower channel pattern structures 435. The specimen is able to pass through the porous membrane 450 and flow between the channel chip 430 and the split chip 440 to make the circulating tumor cell be captured by the porous membrane 450. Specifically, a pore diameter of the porous membrane 450 can be 5-12 micrometer to efficiently capture the circulating tumor cell. In addition, the material of the porous membrane 450 can be, but not limited to, a materials that is easily processed, such as polycarbonate, polyethylene terephthalate, polypropylene and poly(dimethylsiloxane).

Furthermore, as shown in FIG. 4B, the chip system 400 further includes the first layer cover 460 and the second layer cover 470. When the channel chip 430 and the porous membrane 450 embedded between the upper channel pattern structure 434 and the lower channel pattern structure 435 are detached for performing the drug sensitivity analysis, the first layer cover 460 and the second layer cover 470 are sequentially stacked on the channel chip 430. Specifically, the structure and the material of the first layer cover 460 can be the same as the channel chip 430. The structure of the second layer cover 470 can cover all the hollow portions of the first layer cover 460.

Method for Circulating Tumor Cell Capture

Figure 5:
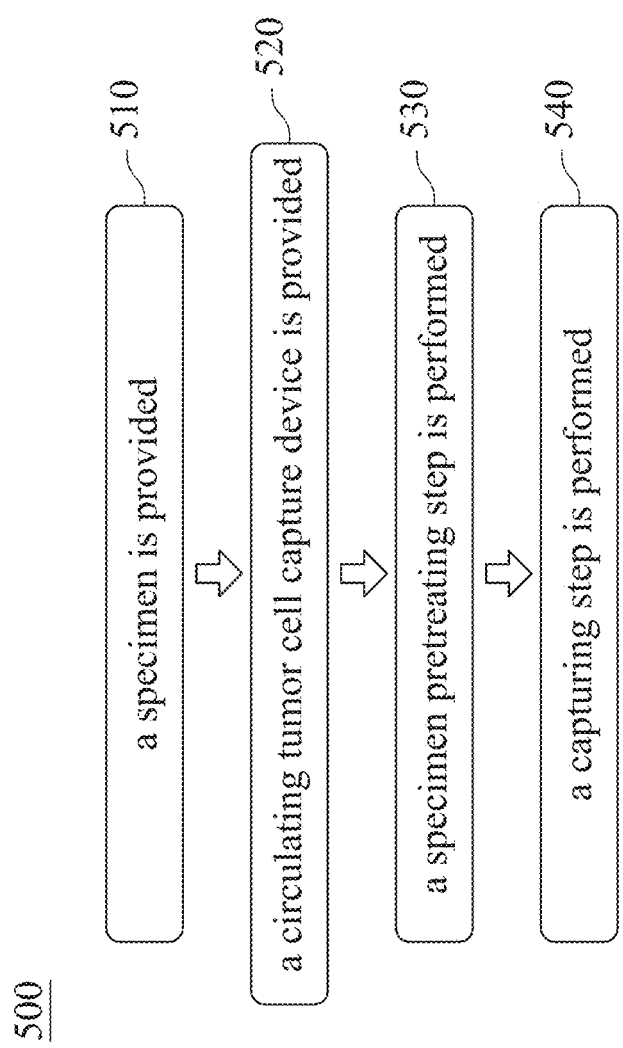
FIG. 5 is a flow chart of one example according to another embodiment of a method for circulating tumor cell capture of the present disclosure.

FIG. 5 is a flow chart of one example according to another embodiment of a method for circulating tumor cell capture 500 of the present disclosure. The following explanation depends on the circulating tumor cell capture device 100 of FIG. 1 and the chip system 300 of FIG. 2. The method for circulating tumor cell capture 500 includes Step 510, Step 520, Step 530 and Step 540.

In Step 510, a specimen is provided. The specimen can be a blood specimen, especially a whole blood specimen, from a subject.

In Step 520, the circulating tumor cell capture device 100 is provided. Please refer to FIG. 1 and FIG. 2 for the detailed structure of the circulating tumor cell capture device 100, and unnecessary details will not be given here.

In Step 530, a specimen pretreating step is performed. The specimen pretreating step is to reduce an amount of blood cells in the specimen, in order to obtain a separated specimen with the circulating tumor cell. The blood cells include platelets, red blood cells and leukocytes. When reducing the amount of blood cells in the specimen, immunomagnetic beads of CD45 and CD36 are used to bind to leukocytes in the specimen, and then the leukocytes bound to immunomagnetic beads are removed. The amount of platelets and red blood cells in the specimen can be reduced by applying the methods such as centrifuging. Specifically, the specimen pretreating step includes steps as follows. A blood collection tube with anticoagulation factors is used to collect enough specimen, and the specimen is centrifuged at 1200×g of rotor speed and room temperature for 20 minutes. The supernatant is removed. Then, buffer solution, RosetteSep™ Human CD45 Depletion Cocktail (STEMCELL) and RosetteSep™ Human Monocyte Depletion Cocktail (STEMCELL) are added to the blood cells at the bottom of the blood collection tube. After being evenly mixed for 20 minutes by shaking, the specimen is centrifuged at 1200×g of rotor speed for 20 minutes and separated into three layers. A separated specimen with the circulating tumor cell can be obtained from the middle layer of the specimen.

In Step 540, a capturing step is performed. The capturing step is to draw the separated specimen into the specimen entrance 313, and make the separated specimen flow between the channel chip 330 and the split chip 340 and pass through the porous membrane 350 by the pump 200, in order to make the circulating tumor cell be captured by the porous membrane 350. Specifically, a draw-in rate of the pump 200 making the separated specimen flow between the channel chip 330 and the split chip 340 is 0.5 ml/min to 10 ml/min.

Figure 6:
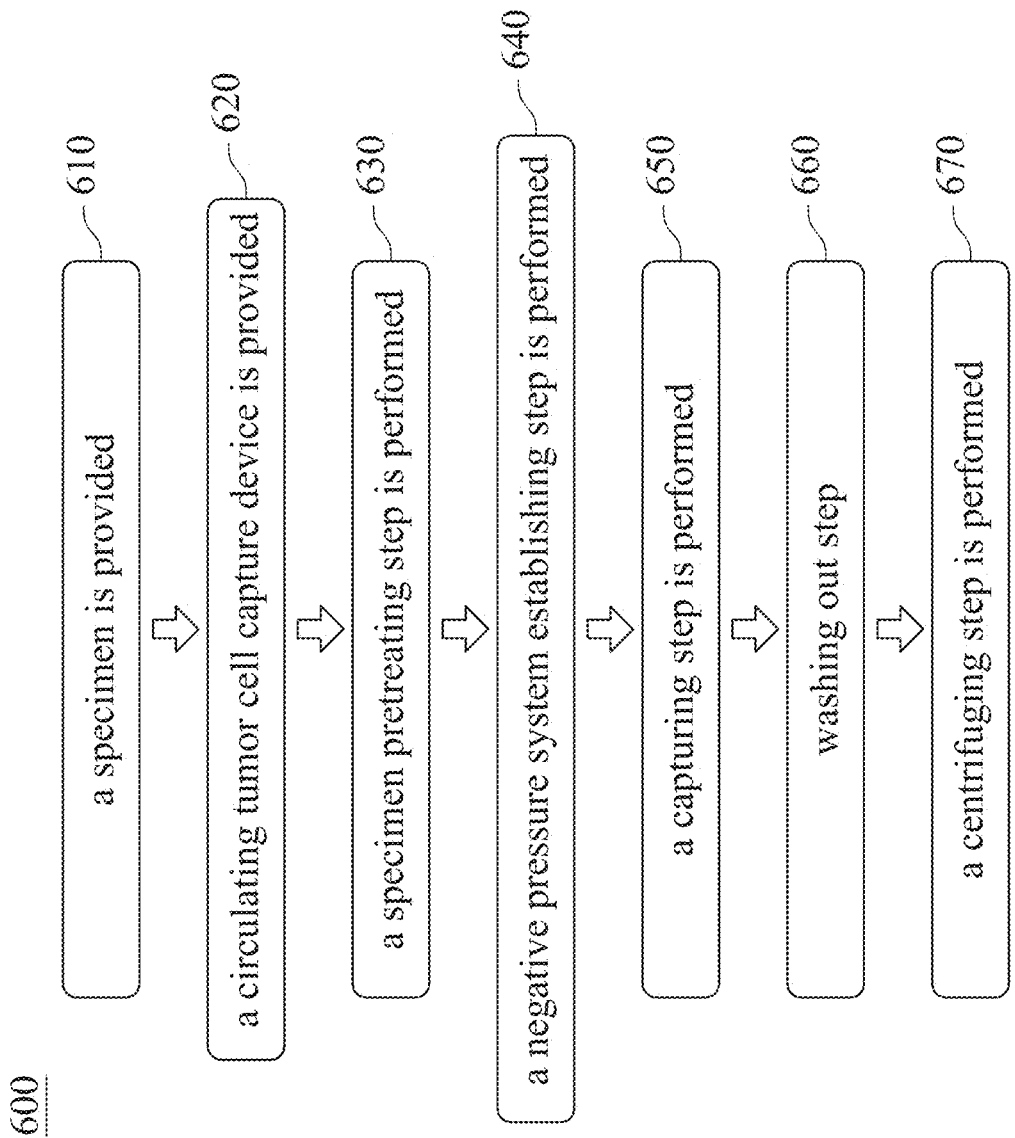
FIG. 6 is a flow chart of another example according to another embodiment of a method for circulating tumor cell capture of the present disclosure.

FIG. 6 is a flow chart of another example according to another embodiment of a method for circulating tumor cell capture 600 of the present disclosure. The following explanation depends on the circulating tumor cell capture device 100 of FIG. 1 and the chip system 300 of FIG. 2. The method for circulating tumor cell capture 600 includes Step 610, Step 620, Step 630, Step 640, Step 650, Step 660 and Step 670.

In Step 610, a specimen is provided. The specimen can be a blood specimen, especially a whole blood specimen, from a subject.

In Step 620, the circulating tumor cell capture device 100 is provided. Please refer to FIG. 1 and FIG. 2 for the detailed structure of the circulating tumor cell capture device 100, and unnecessary details will not be given here.

In Step 630, a specimen pretreating step is performed. The details of the specimen pretreating step have been described in Step 530, and unnecessary details will not be given here.

In Step 640, a negative pressure system establishing step is performed. The negative pressure system establishing step is to pump a buffer solution into the specimen exit 314 by the pump 200, in order to evacuate the air in the chip system 300. Therefore, the chip system 300 is filled with liquid.

In Step 650, a capturing step is performed. The details of the capturing step have been described in Step 540, and unnecessary details will not be given here.

In Step 660, a washing out step is performed. The washing out step is to pump a buffer solution into the specimen exit 314 by the pump 200, and a separated solution is collected at the specimen entrance 313. Specifically, a wash-out rate of the pump 200 is 0.5 ml/min to 10 ml/min.

In Step 670, a centrifuging step is performed. The centrifuging step is to centrifuge the separated solution to obtain the isolated circulating tumor cell. Specifically, the centrifugal force is 1200×g and the centrifuging time is 5 minutes in the centrifuging step. In this regard, the isolated circulating tumor cell obtained is still alive, and can be further cultured into a large-scale or established a cell line, which is convenient for follow-up analyses such as oncogene analysis.

Method for Circulating Tumor Cell Capture and Drug Sensitivity Analysis

Figure 7:
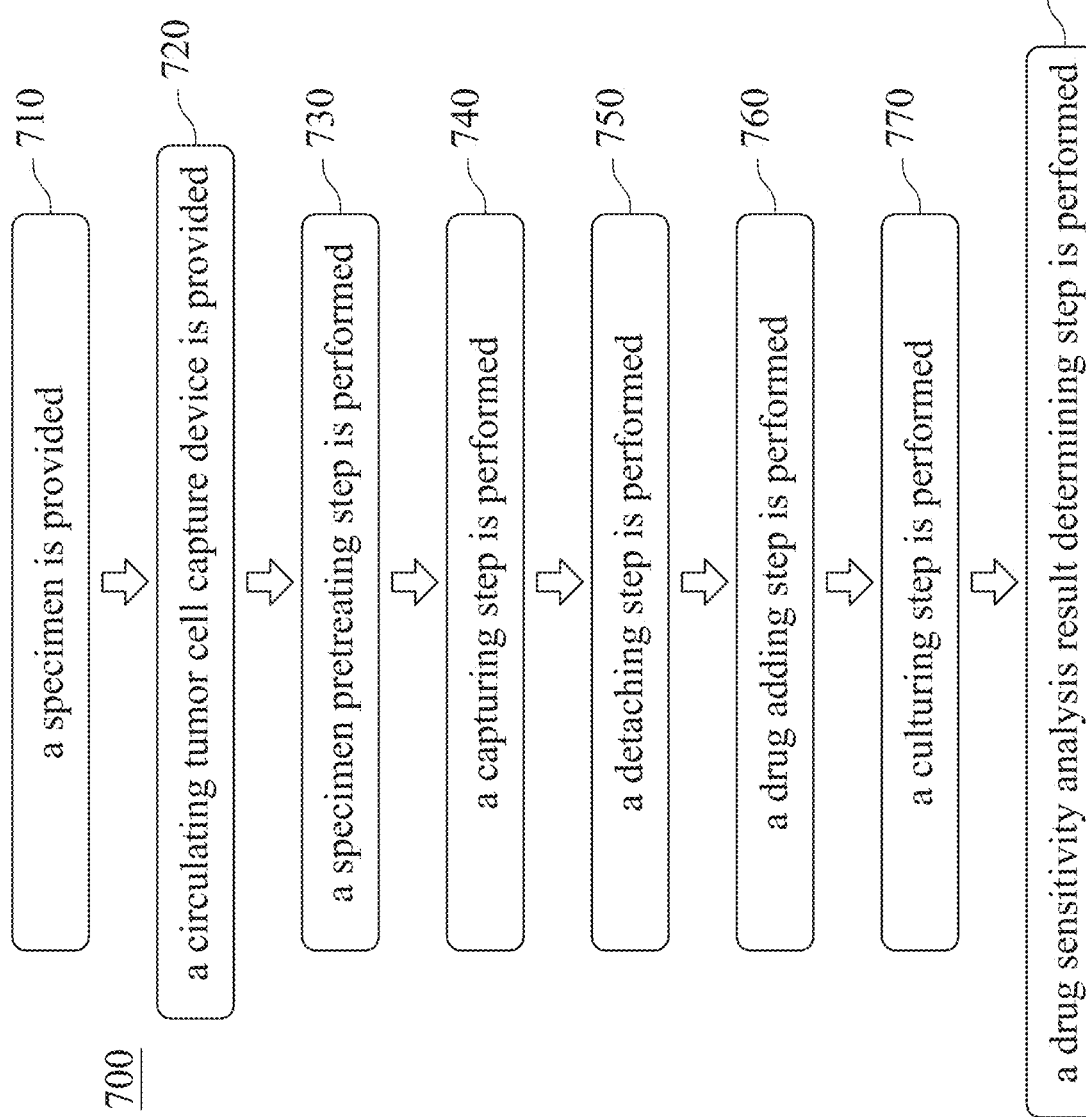
FIG. 7 is a flow chart of one example according to still another embodiment of a method for circulating tumor cell capture and drug sensitivity analysis of the present disclosure.
Figure 8:
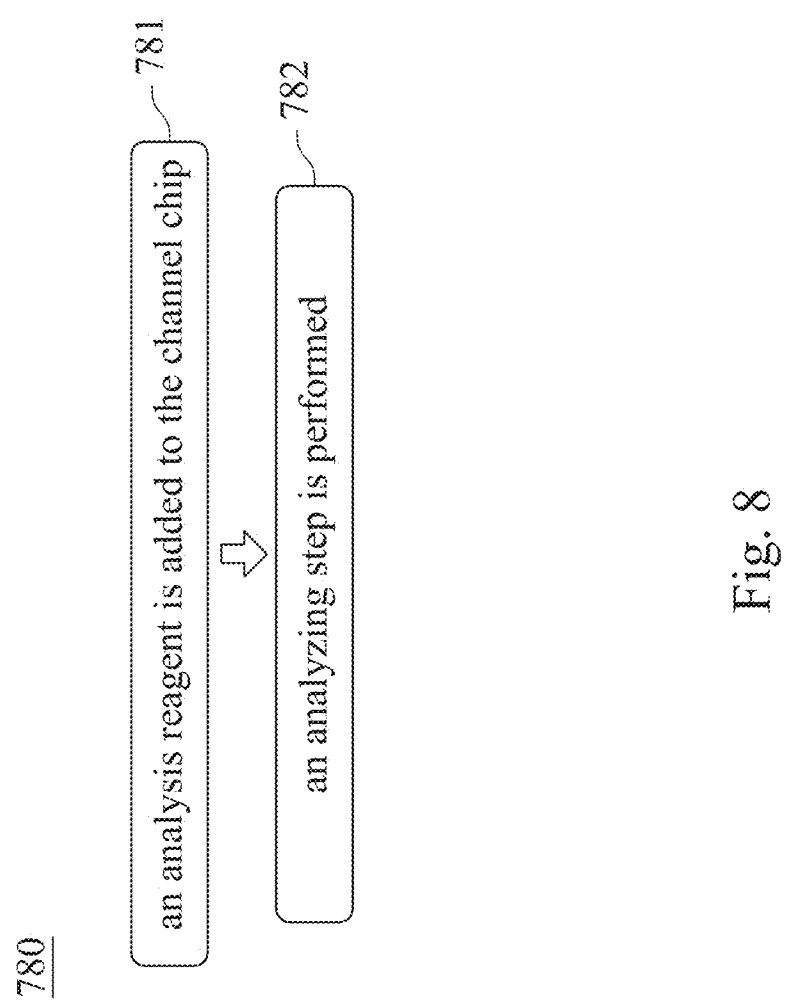
FIG. 8 is a detailed flow chart of Step 780 in FIG. 7.

Please refer to FIG. 7 and FIG. 8. FIG. 7 is a flow chart of one example according to still another embodiment of a method for circulating tumor cell capture and drug sensitivity analysis 700 of the present disclosure. FIG. 8 is a detailed flow chart of Step 780 in FIG. 7. The following explanation depends on the circulating tumor cell capture device 100 of FIG. 1 and the chip system 400 of FIG. 4A. The method for circulating tumor cell capture and drug sensitivity analysis 700 includes Step 710, Step 720, Step 730, Step 740, Step 750, Step 760, Step 770 and Step 780.

In Step 710, a specimen is provided. The specimen can be a blood specimen, especially a whole blood specimen, from a subject.

In Step 720, the circulating tumor cell capture device 100 is provided. Please refer to FIG. 1, FIG. 4A and FIG. 4B for the detailed structure of the circulating tumor cell capture device 100.

In Step 730, a specimen pretreating step is performed. The details of the specimen pretreating step have been described in Step 530, and unnecessary details will not be given here.

In Step 740, a capturing step is performed. The capturing step is to draw the separated specimen into the specimen entrance 413, and make the separated specimen flow between the channel chip 430 and the split chip 440 and pass through the porous membrane 450 by the pump 200, in order to make the circulating tumor cell be captured by the porous membrane 450. Specifically, a draw-in rate of the pump 200 making the separated specimen flow between the channel chip 430 and the split chip 440 is 0.5 ml/min to 10 ml/min.

In Step 750, a detaching step is performed. The detaching step is to detach the lower chip set 420 from the chip system 400.

In Step 760, a drug adding step is performed. The drug adding step is to detach the channel chip 430 from the lower chip set 420, and to add at least one testing drug on the channel chip 430. Specifically, the at least one testing drug can be four different kinds of drugs for simultaneous multiple drug testing. Optionally, the at least one testing drug can be the same drug with four different concentrations, such as the drugs prepared by serial dilution, in order to determine a minimal concentration of the circulating tumor cell being resistant to the drug. For instance, cisplatin can be used as determining the minimal concentration of the circulating tumor cell being resistant to the drug.

In Step 770, a culturing step is performed. The culturing step is to culture the channel chip 430 with the at least one testing drug added under a culture condition for a culture time. Specifically, the channel chip 430 can be placed in a 3.5 mm petri dish and cultured for 24 hours in an incubator with an environment of 5% $CO_2$ and 37° C.

In Step 780, a drug sensitivity analysis result determining step is performed. In detail, the drug sensitivity analysis result determining step includes Step 781 and Step 782. In Step 781, an analysis reagent is added to the channel chip 430. In Step 782, an analyzing step is performed to determine whether the circulating tumor cell is resistant to the at least one testing drug or not.

Specifically, the analysis reagent added in Step 781 can be a Live/Dead cell viability assay kit. Then, whether the circulating tumor cell is alive or not is analyzed by a fluorescence microscope in Step 782, in order to determine whether the circulating tumor cell is resistant to the at least one testing drug or not. If the circulating tumor cell is alive, the observed cell will be green in the fluorescence microscope under the condition of Ex/Em=485/535 nm. If the circulating tumor cell is dead, the observed cell will be red in the fluorescence microscope under the condition of Ex/Em=495/635 nm.

Furthermore, the drug sensitivity analysis result determining Step 780 is also for determining a minimal concentration range of the circulating tumor cell being resistant to the at least one testing drug. Specifically, in order to determine a minimal concentration range of the circulating tumor cell being resistant to the at least one testing drug, the testing drugs added in Step 760 include a control group and three drugs prepared by serial dilution for comparison, and $IC_{50}$ is adopted for analyzing in Step 782.

Figure 9:
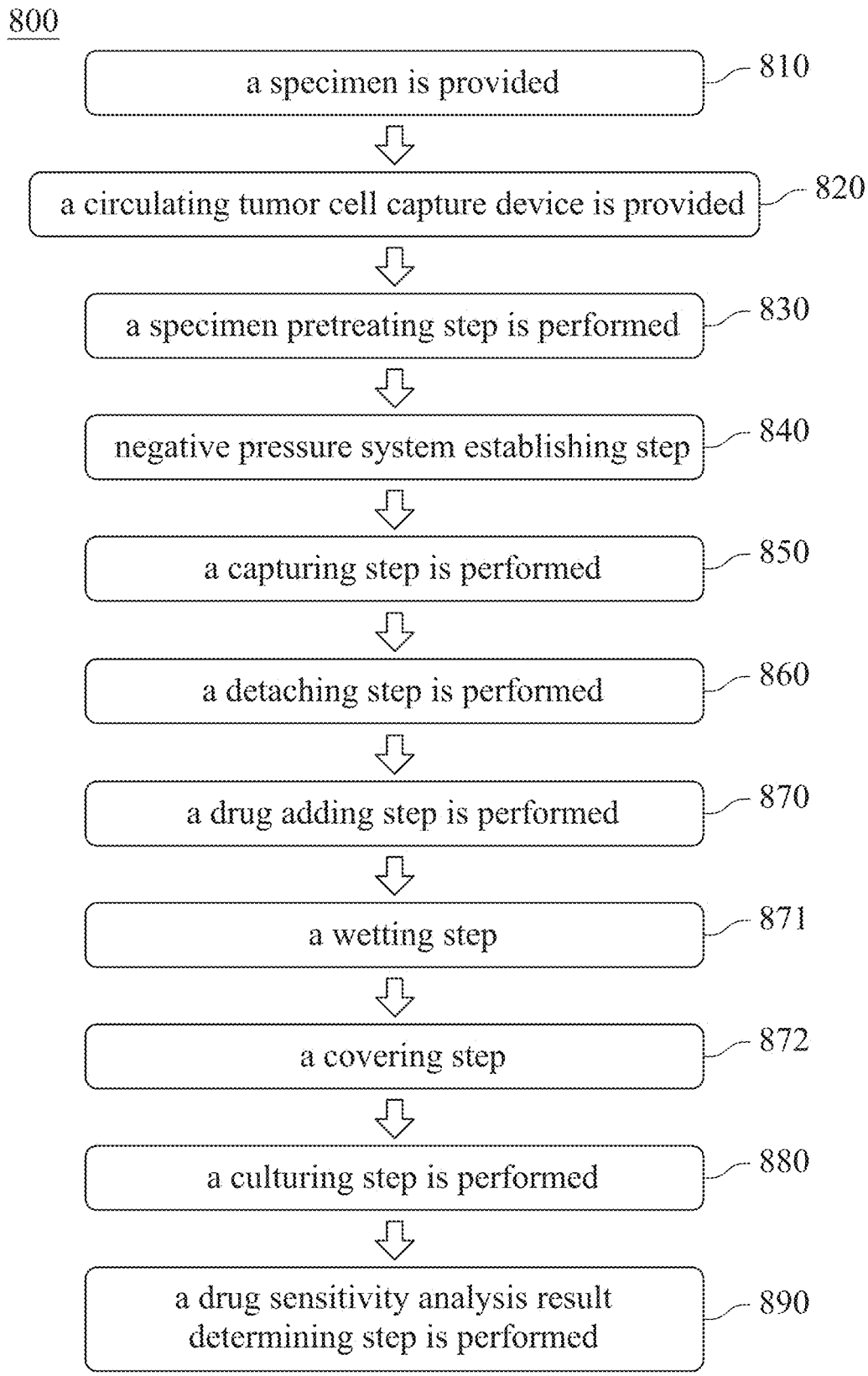
FIG. 9 is a flow chart of a drug sensitivity analysis result determining step of another example according to still another embodiment of the present disclosure.

FIG. 9 is a flow chart of another example according to still another embodiment of a method for circulating tumor cell capture and drug sensitivity analysis 800 of the present disclosure. The following explanation depends on the circulating tumor cell capture device 100 of FIG. 1 and the chip system 400 of FIG. 4A and FIG. 4B. The method for circulating tumor cell capture and drug sensitivity analysis 800 includes Step 810, Step 820, Step 830, Step 840, Step 850, Step 860, Step 870, Step 880 and Step 890.

In Step 810, a specimen is provided. The specimen can be a blood specimen, especially a whole blood specimen, from a subject.

In Step 820, the circulating tumor cell capture device 100 is provided. Please refer to FIG. 1, FIG. 4A and FIG. 4B for the detailed structure of the circulating tumor cell capture device 100.

In Step 830, a specimen pretreating step is performed. The details of the specimen pretreating step have been described in Step 530, and unnecessary details will not be given here.

In Step 840, a negative pressure system establishing step is performed. The negative pressure system establishing step is to pump a buffer solution into the specimen exit (not shown) by the pump 200, in order to evacuate the air in the chip system 400. Therefore, the chip system 400 is filled with liquid.

In Step 850, a capturing step is performed. The details of the capturing step have been described in Step 740, and unnecessary details will not be given here.

In Step 860, a detaching step is performed. The detaching step is to detach the lower chip set 420 from the chip system 400.

In Step 870, a drug adding step is performed. The drug adding step is to detach the channel chip 430 from the lower chip set 420, and to add at least one testing drug on the channel chip 430. Specifically, the at least one testing drug can be four different kinds of drugs for simultaneous multiple drug testing. Optionally, the at least one testing drug can be the same drug with four different concentrations, such as the drugs prepared by serial dilution, in order to determine a minimal concentration of the circulating tumor cell being resistant to the drug. In addition, the drug adding step further includes a wetting step and a covering step.

In Step 871, the wetting step is performed. Please refer to FIG. 4B, the wetting step is to stack a first layer cover 460 on the channel chip 430, and to draw the at least one testing drug into the first layer cover 460. Specifically, the structure of the first layer cover 460 can be the same as the channel chip 430.

In Step 872, the covering step is performed. Please refer to FIG. 4B, the covering step is to stack a second layer cover 470 on the first layer cover 460. In this regard, the amount of solvent of the testing drug is increased, and the testing drug is prevented from vaporizing out.

In Step 880, a culturing step is performed. The culturing step is to culture the channel chip 430 with the at least one testing drug added under a culture condition for a culture time. Specifically, the channel chip 430 can be placed in a 3.5 mm petri dish and cultured for 24 hours in an incubator with an environment of 5% $CO_2$ and 37° C.

In Step 890, a drug sensitivity analysis result determining step is performed. The details of the drug sensitivity analysis result determining step have been described in Step 780, Step 781 and Step 782, and unnecessary details will not be given here.

Efficiency of Capturing Circulating Tumor Cell

The following experiment will first discuss the effect on the efficiency of capturing circulating tumor cell of the circulating tumor cell capture device according to the present disclosure, which is resulted from different testing conditions. The different testing conditions for discussion include the number of the upper channel pattern structure and the lower channel pattern structure, the pore diameter of the porous membrane, the wash-out rate and the draw-in rate.

The testing cancer cell for the experiment is A549 cell. The medium for culturing A549 cell is a Dulbecco's modified Eagle's medium (DMEM) containing 10% of fetal bovine serum (FBS) and 1% of antibiotic solution. The specimen used in the experiment includes 5 ml of the medium and $3 \times 10^4$ A549 cells.

To discuss the effect resulted from the number of the upper channel pattern structure and the lower channel pattern structure, the experimental steps are as follows: first, a buffer solution is pumped into the specimen exit by the pump, in order to evacuate the air in the chip system. Then, the specimen is drawn into the specimen entrance with a rate of 1.5 ml/min by the pump, in order to make the circulating tumor cell be captured by the porous membrane with the pore diameter of 8 micrometer. Then, a buffer solution is pumped into the specimen exit with a rate of 5 ml/min by the pump, and a separated solution is collected at the specimen entrance. Finally, the separated solution is centrifuged at 1200×g of rotor speed and room temperature for 20 minutes, and drawn out for observation.

Figure 10A:
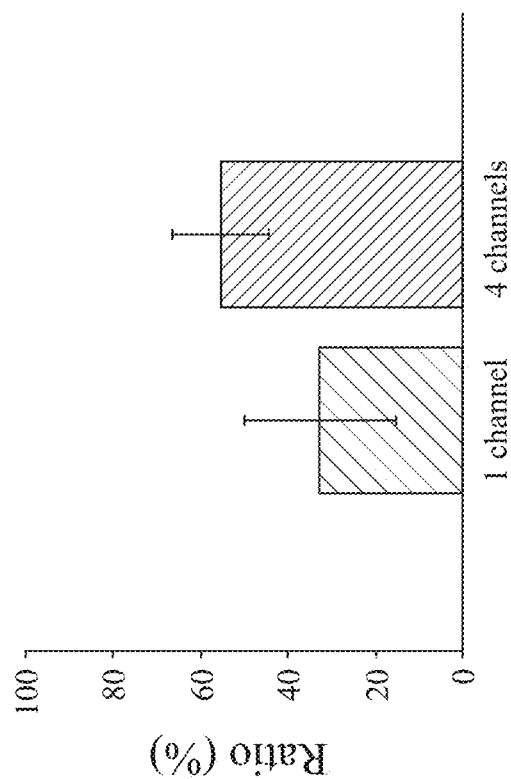
FIG. 10A is a result graph showing a number of an upper channel pattern structure and a lower channel pattern structure of the channel chip and ratios of cells passing through the porous membrane.
Figure 10B:
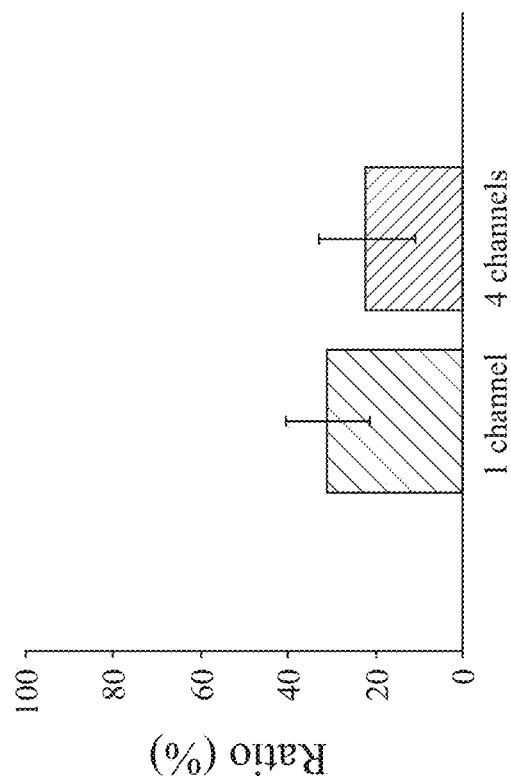
FIG. 10B is a result graph showing the number of the upper channel pattern structure and the lower channel pattern structure of the channel chip and ratios of cells being captured.

Please refer to FIG. 10A and FIG. 10B. FIG. 10A is a result graph showing the number of the upper channel pattern structure and the lower channel pattern structure of the channel chip and ratios of cells passing through the porous membrane. FIG. 10B is a result graph showing the number of the upper channel pattern structure and the lower channel pattern structure of the channel chip and ratios of cells being captured. In FIG. 10A and FIG. 10B, when the number of the upper channel pattern structure and the lower channel pattern structure is 1, respectively, the fluidic pressure in the channel is relatively large, which makes the cells relatively easy to pass through the porous membrane. However, the ratio of A549 cells being captured is not higher than 40%. When the number of the upper channel pattern structure and the lower channel pattern structure is 4, respectively, the capture efficiency is enhanced to 60% due to larger separating area.

To discuss the effect resulted from the pore diameter of the porous membrane, the experimental steps are as follows: first, a buffer solution is pumped into the specimen exit by the pump, in order to evacuate the air in the chip system. Then, the specimen is drawn into the specimen entrance with a rate of 1.5 ml/min by the pump, in order to make the circulating tumor cell be captured by the porous membrane with the pore diameter of 5 micrometer or 8 micrometer. Then, a buffer solution is pumped into the specimen exit with a rate of 5 ml/min by the pump, and a separated solution is collected at the specimen entrance. Finally, the separated solution is centrifuged at 1200×g of rotor speed and room temperature for 20 minutes, and drawn out for observation.

Figure 11B:
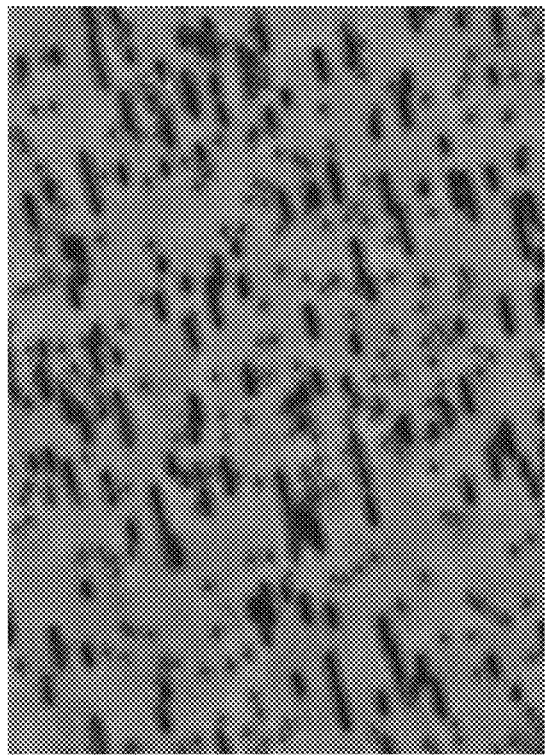
FIG. 11B is a microscopic image of the porous membrane of another example.
Figure 11A:
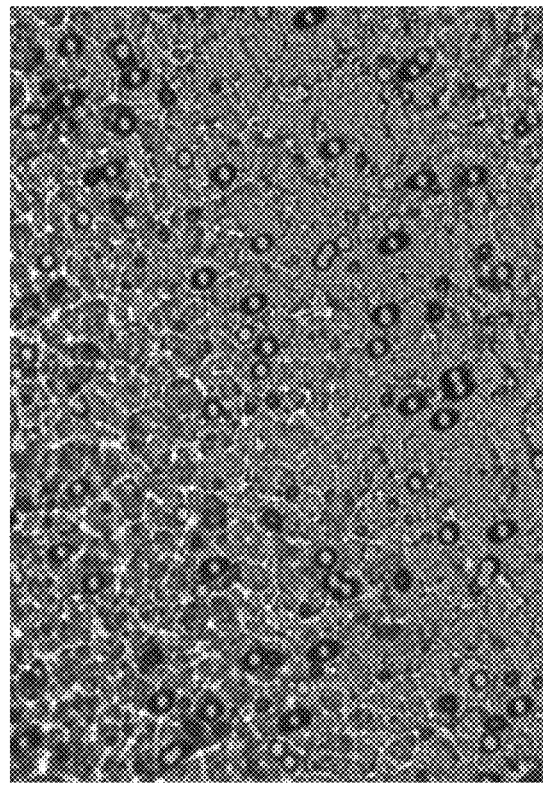
FIG. 11A is a microscopic image of the porous membrane of one example.
Figure 12B:
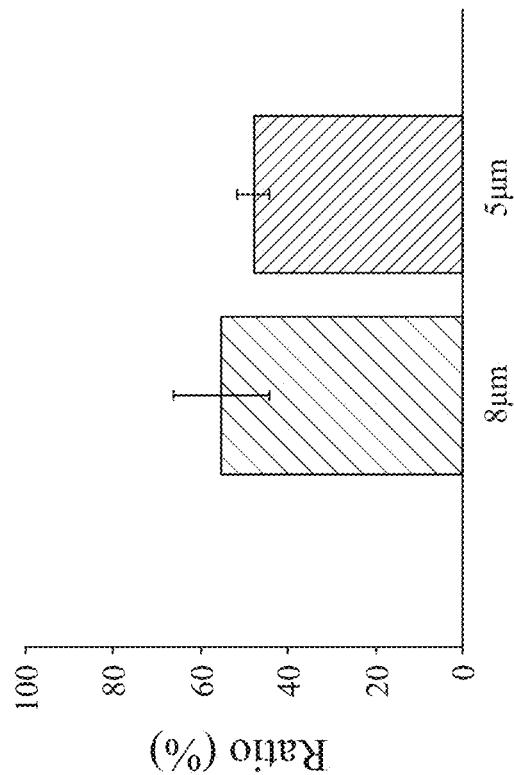
FIG. 12B is a result graph showing the ratios of testing cancer cells being captured by the porous membranes of different examples.
Figure 12A:
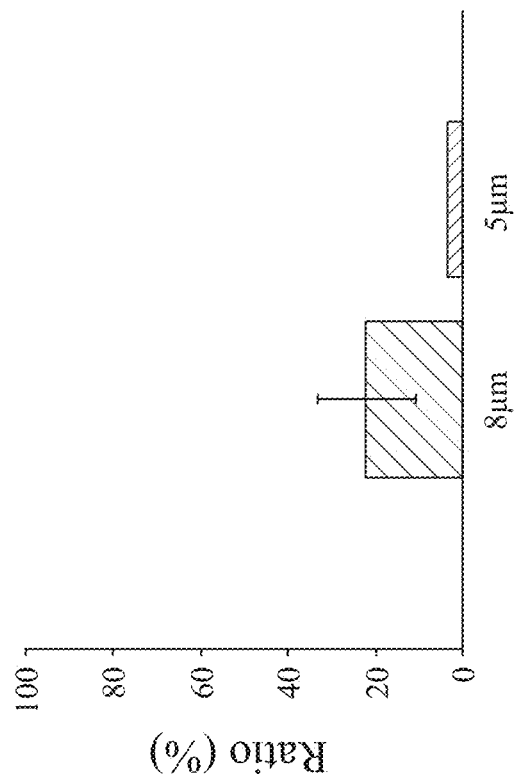
FIG. 12A is a result graph showing the ratios of testing cancer cells passing through the porous membranes of different examples.

Please refer to FIG. 11A, FIG. 11B, FIG. 12A and FIG. 12B. FIG. 11A is a microscopic image of the porous membrane of one example. FIG. 11B is a microscopic image of the porous membrane of another example. FIG. 12A is a result graph showing the ratios of testing cancer cells passing through the porous membranes of different examples. FIG. 12B is a result graph showing the ratios of testing cancer cells being captured by the porous membranes of different examples. In FIG. 12A and FIG. 12B, when using the porous membrane with the pore diameter of 5 micrometer, the ratio of A549 cells passing through the porous membrane is relatively low and the experimental result is below 4%. Besides, the A549 cells can be squeezed to pass through the porous membrane, because the porous membrane with the pore diameter of 8 micrometer has larger pores than the porous membrane with the pore diameter of 5 micrometer. Thus, the ratio of A549 cells passing through the porous membrane with the pore diameter of 8 micrometer is relatively high and the experimental result is 20%. However, the A549 cells are liable to stuck on the porous membrane with the pore diameter of 5 micrometer, and are difficult to be washed out in the washing out step. Thus, the ratio of A549 cells being captured by the porous membrane with the pore diameter of 8 micrometer is higher than the ratio of A549 cells being captured by the porous membrane with the pore diameter of 5 micrometer.

Moreover, to discuss the effect resulted from different wash-out rate of the pump, the experimental steps are as follows: first, a buffer solution is pumped into the specimen exit by the pump, in order to evacuate the air in the chip system. Then, the specimen is drawn into the specimen entrance with a rate of 1.5 ml/min by the pump, in order to make the circulating tumor cell be captured by the porous membrane with the pore diameter of 8 micrometer. Then, a buffer solution is pumped into the specimen exit with a rate of 2 ml/min, 3.5 ml/min or 5 ml/min by the pump, and a separated solution is collected at the specimen entrance. Finally, the separated solution is centrifuged at 1200×g of rotor speed and room temperature for 20 minutes, and drawn out for observation.

Figure 13:
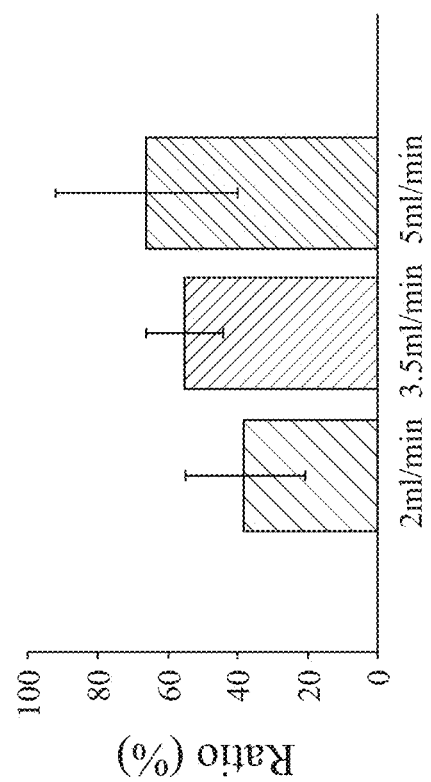
FIG. 13 is a result graph showing the ratios of testing cancer cells being captured under different wash-out rates of the pump.

Please refer to FIG. 13. FIG. 13 is a result graph showing the ratios of testing cancer cells being captured under different wash-out rates of the pump. In FIG. 13, when the wash-out rate is faster, the ratio of A549 cells being captured is enhanced. The wash-out rate of 5 ml/min results in the highest ratio of A549 cells being captured, and the experimental result is up to 70%.

Furthermore, to discuss the effect resulted from different draw-in rate of the pump, the experimental steps are as follows: first, a buffer solution is pumped into the specimen exit by the pump, in order to evacuate the air in the chip system. Then, the specimen is drawn into the specimen entrance with a rate of 1.5 ml/min, 3.5 ml/min or 5 ml/min by the pump, in order to make the circulating tumor cell be captured by the porous membrane with the pore diameter of 8 micrometer. Then, a buffer solution is pumped into the specimen exit with a rate of 5 ml/min by the pump, and a separated solution is collected at the specimen entrance. Finally, the separated solution is centrifuged at 1200×g of rotor speed and room temperature for 20 minutes, and drawn out for observation.

Figure 14B:
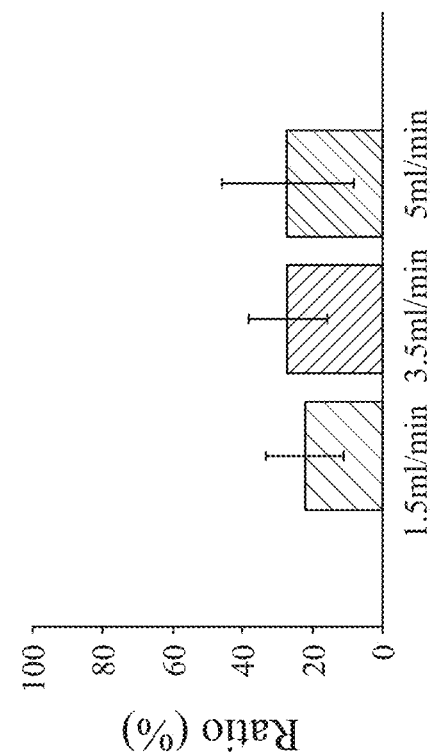
FIG. 14B is a result graph showing the ratios of testing cancer cells being captured under different draw-in rates of the pump.
Figure 14A:
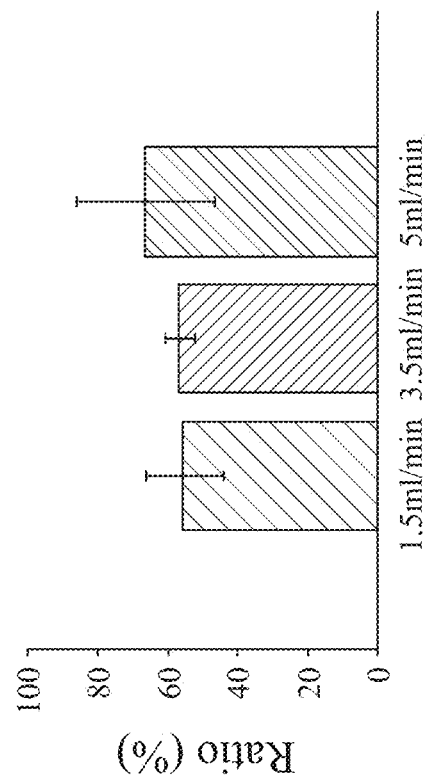
FIG. 14A is a result graph showing the ratios of testing cancer cells passing through the porous membrane under different draw-in rates of the pump.

Please refer to FIG. 14A and FIG. 14B. FIG. 14A is a result graph showing the ratios of testing cancer cells passing through the porous membrane under different draw-in rates of the pump. FIG. 14B is a result graph showing the ratios of testing cancer cells being captured under different draw-in rates of the pump. In FIG. 14A and FIG. 14B, different draw-in rates of the pump barely affect the ratios of A549 cells passing through the porous membrane and the ratios of A549 cells being captured. The experimental results are the same as the mentioned ratio of A549 cells being captured of 60%.

Confirming Experiment for Washed-Out Circulating Tumor Cell after being Captured Testing Cancer Cell for Specimen The specimen used in following experiments includes 5 ml medium and $3 \times 10^4$ A549 cells.

The experimental steps are as follows: first, a buffer solution is pumped into the specimen exit by the pump, in order to evacuate the air in the chip system. Then, the specimen is drawn into the specimen entrance with a rate of 1.5 ml/min by the pump, in order to make the circulating tumor cell be captured by the porous membrane with the pore diameter of 8 micrometer. Then, a buffer solution is pumped into the specimen exit with a rate of 5 ml/min by the pump, and a separated solution is collected at the specimen entrance. Finally, the separated solution is centrifuged at 1200×g of rotor speed and room temperature for 20 minutes, and drawn out for microscopy observation.

Figure 15B:
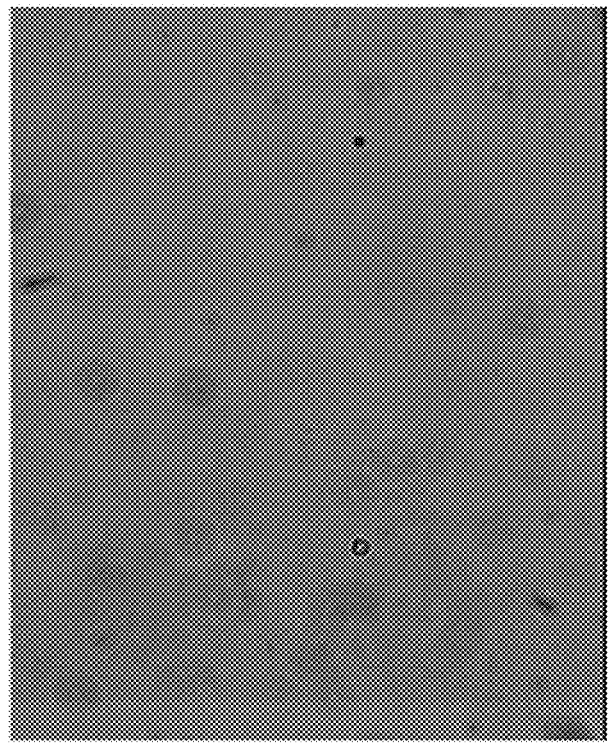
FIG. 15B is a microscopic image of the testing cancer cells passing through the porous membrane.
Figure 15A:
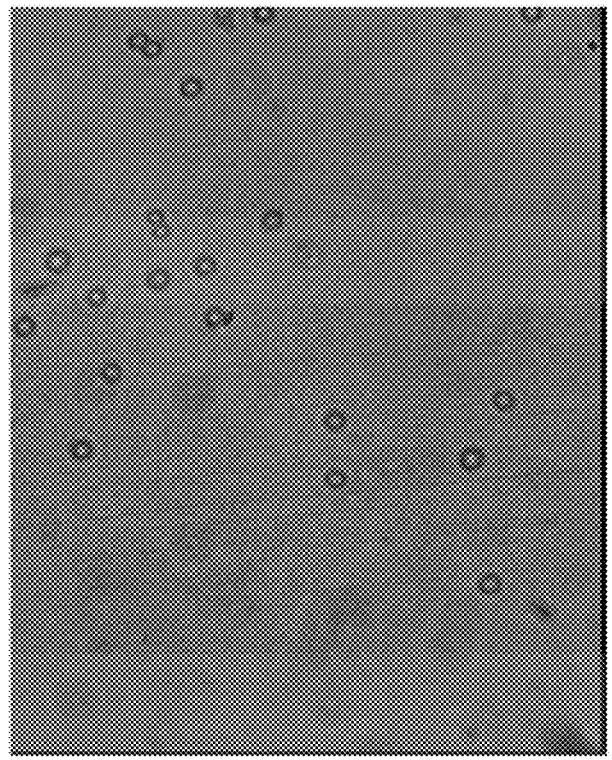
FIG. 15A is a microscopic image of the testing cancer cells washed out after being captured.

Please refer to FIG. 15A and FIG. 15B. FIG. 15A is a microscopic image of the testing cancer cells washed out after being captured. FIG. 15B is a microscopic image of the testing cancer cells passing through the porous membrane. FIG. 15A and FIG. 15B are taken right after the cells separated by the centrifuging step. It is realized that all the A549 cells are in suspension, and the amount of A549 cells being captured is greatly larger than the amount of A549 cells passing through the porous membrane.

Figure 16A:
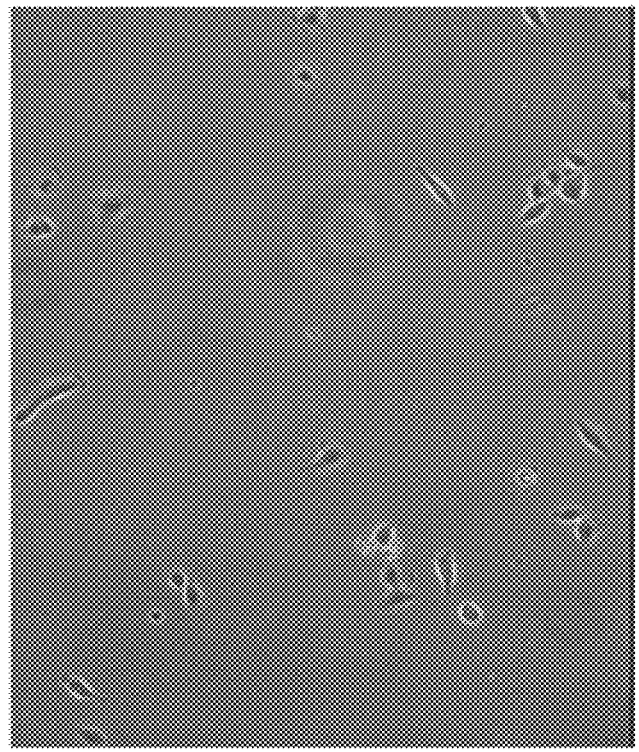
FIG. 16A is a microscopic image of the testing cancer cells washed out after being captured and cultured for 1 day.
Figure 16B:
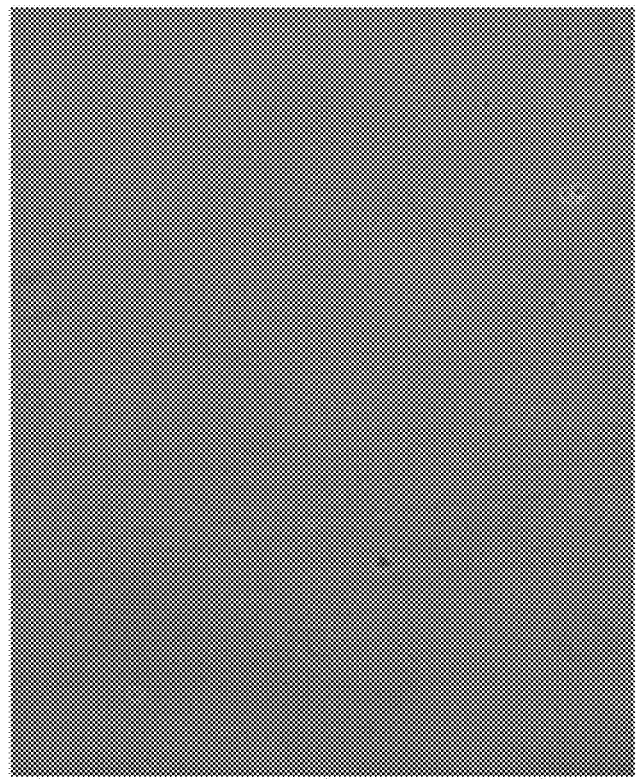
FIG. 16B is a microscopic image of the testing cancer cells passing through the porous membrane and after being cultured for 1 day.

Please refer to FIG. 16A and FIG. 16B. FIG. 16A is a microscopic image of the testing cancer cells washed out after being captured and cultured for 1 day. FIG. 16B is a microscopic image of the testing cancer cells passing through the porous membrane and after being cultured for 1 day. In FIG. 16A and FIG. 16B, most of the A549 cells being captured adhere to the petri dish after being washed out and cultured for 1 day, which represents that the testing cancer cells washed out are alive. However, there is no living A549 cells, which pass through the porous membrane and are cultured for 1 day, on the petri dish. Therefore, it represents that the A549 cells captured by the chip system 300 is capable of being cultured again.

Real Blood for Specimen

The specimen used in following experiments is real blood, which is prepared by mixing the whole blood from healthy adult with A549 cells to replace a blood specimen from cancer patient. The mentioned real blood includes 5 ml serum, leukocytes obtained from the whole blood from healthy adult by the specimen pretreating step, and A549 cells. Specifically, the real blood having A549 cells includes $3\times10^4$ leukocytes and $3\times10^4$ A549 cells.

The experimental steps are as follows: first, a buffer solution is pumped into the specimen exit by the pump, in order to evacuate the air in the chip system. Then, the specimen is drawn into the specimen entrance with a rate of 1.5 ml/min by the pump, in order to make the circulating tumor cell be captured by the porous membrane with the pore diameter of 8 micrometer. Then, a buffer solution is pumped into the specimen exit with a rate of 5 ml/min by the pump, and a separated solution is collected at the specimen entrance. Finally, the separated solution is centrifuged at 1200×g of rotor speed and room temperature for 20 minutes, and drawn out for microscopy observation.

Figure 17A:
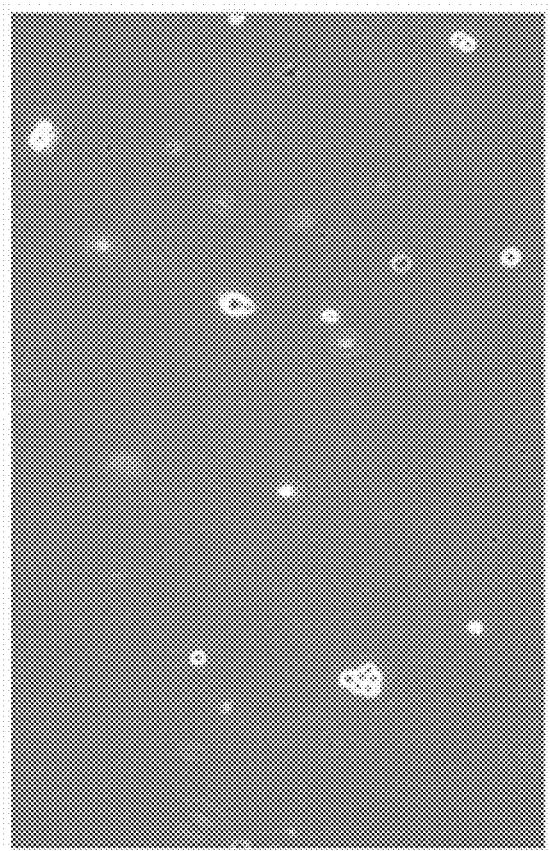
FIG. 17A is a microscopic image of the testing cancer cells washed out after being captured.
Figure 17B:
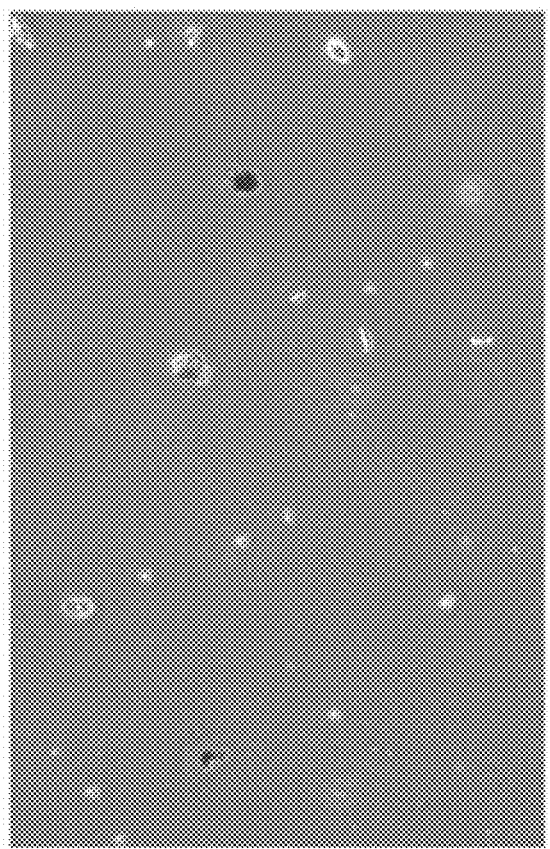
FIG. 17B is a microscopic image of the testing cancer cells passing through the porous membrane.
Figure 18:
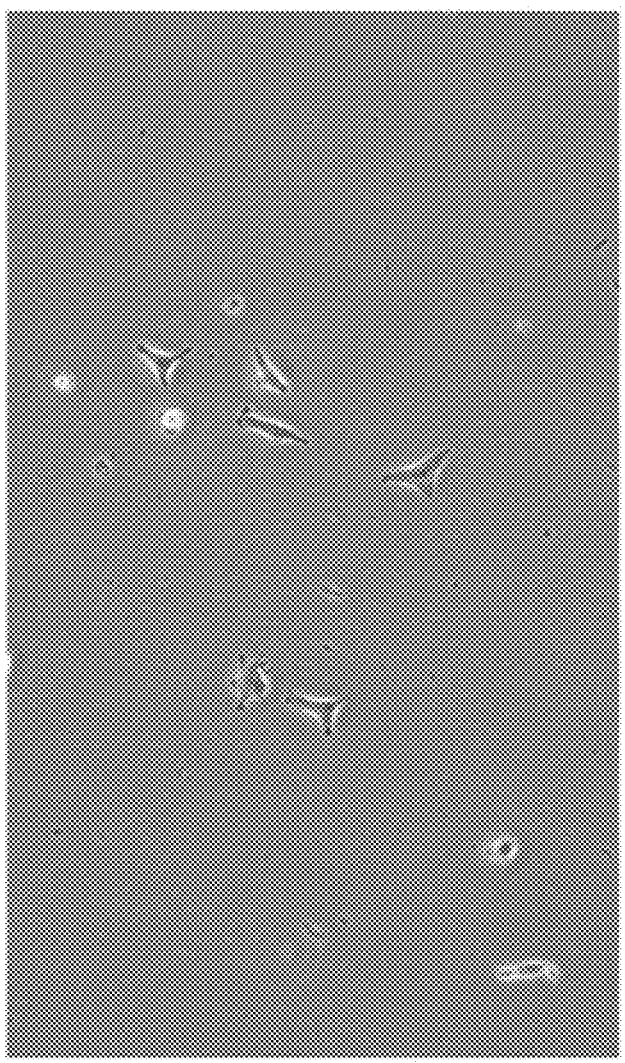
FIG. 18 is a microscopic image of the testing cancer cells washed out after being captured and cultured for 1 day.

Please refer to FIG. 17A, FIG. 17B and FIG. 18. FIG. 17A is a microscopic image of the testing cancer cells washed out after being captured. FIG. 17B is a microscopic image of the testing cancer cells passing through the porous membrane. FIG. 18 is a microscopic image of the testing cancer cells washed out after being captured and cultured for 1 day. In FIG. 17A and FIG. 17B, when the specimen is real blood, a certain amount of A549 cells and a portion of leukocytes are captured. Most of the A549 cells passing through the porous membrane are not living cells (mostly impurities and cell debris). In FIG. 18, the cancer cells captured by the circulating tumor cell capture device and the method thereof according to the present disclosure are capable of being cultured again for further experiments.

Identifying Circulating Tumor Cell Captured by Channel Chip

The specimen used in following experiments includes 5 ml medium and $3\times10^4$ A549 cells.

The experimental steps are as follows: first, a buffer solution is pumped into the specimen exit by the pump, in order to evacuate the air in the chip system. Then, the specimen is drawn into the specimen entrance with a rate of 1.5 ml/min by the pump, in order to make the circulating tumor cell be captured by the porous membrane with the pore diameter of 8 micrometer. Then, the channel chip is detached from the lower chip set, and an analysis reagent is added on the channel chip for microscopy observation.

Figure 19B:
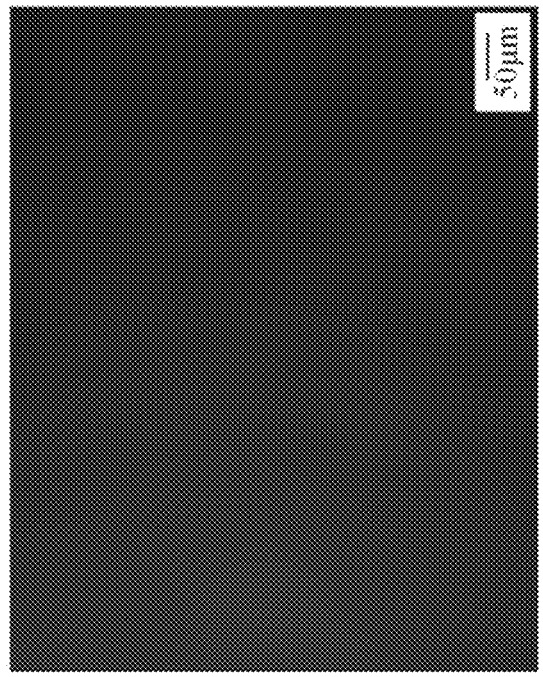
FIG. 19B is a staining result image of observing a split chip by using the fluorescence microscope at 200× magnification.
Figure 19A:
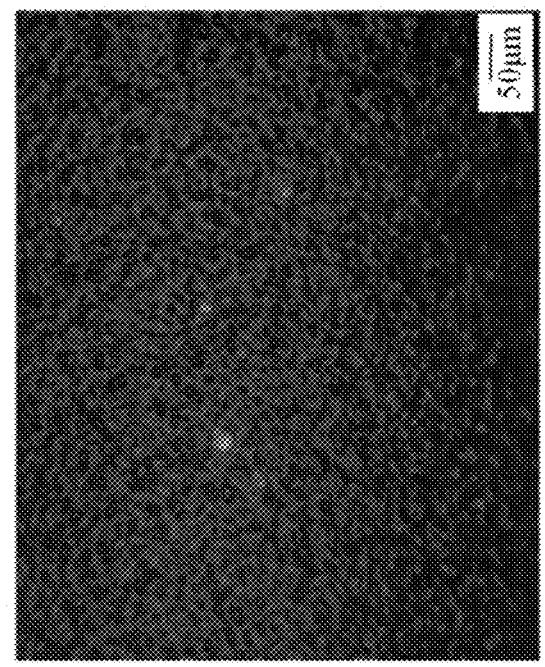
FIG. 19A is a staining result image of the captured testing cancer cells by using a fluorescence microscope at 200× magnification.

Please refer to FIG. 19A, which shows a staining result image of the captured testing cancer cells by using a fluorescence microscope at 200× magnification. In FIG. 19A, 5 cells out of 7 cells are green, which represents the 5 cells are alive. Thus, the circulating tumor cell capture device and the method thereof according to the present disclosure can achieve high viability of A549 cells, and provide a basis for further drug sensitivity analysis. Please refer to FIG. 19B, which is a staining result image of observing the split chip by using the fluorescence microscope at 200× magnification. In FIG. 19B, there is no cell as being colorless. Specifically, A549 cells are all captured by the porous membrane at a side surface of the channel chip away from the split chip.

In addition, the cells captured by the porous membrane are identified by another staining test to investigate the separation effect of circulating tumor cells and leukocytes. The specimen used in this experiments includes 5 ml medium, $3\times10^4$ A549 cells and $3\times10^4$ leukocytes, and other test conditions are as described previously. In another staining test, Hoechst, CD45 and anti-CSV analysis reagents are respectively dropped on the channel chip, and react with the cells under 4° C. and a light preventing environment for 30 minutes before observation.

Figure 20:
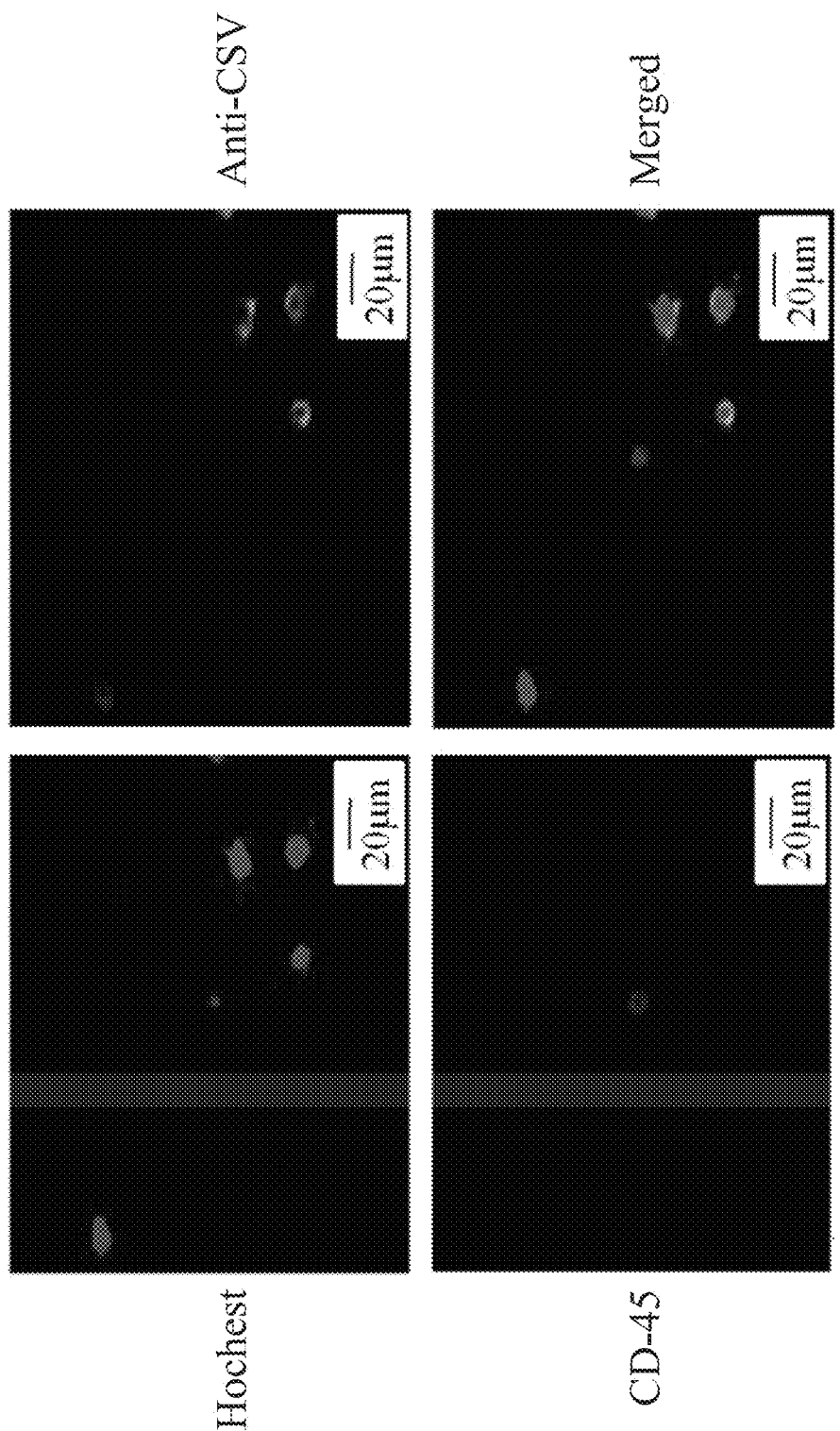
FIG. 20 is a staining result image of captured cells.

Please refer to FIG. 20, which is a staining result image of captured cells. In FIG. 20, because Hoechst is an analysis reagent for staining nucleus, the area with Hoechst expression is identified as a cell. In this result, 5 cells are identified, as well as 4 cells express anti-CSV but not express CD45. As the biomarkers of cancer cells are $CD45^-$ and anti-$CSV^+$, the 4 mentioned cells are all identified as A549 cells. The last cell with biomarkers of $CD45^+$ and anti-$CSV^-$ is identified as leukocyte.

Result of Drug Sensitivity Analysis

The specimen used in following experiments includes 5 ml medium and $3\times10^4$ A549 cells.

The experimental steps are as follows: first, a buffer solution is pumped into the specimen exit by the pump, in order to evacuate the air in the chip system. Then, the specimen is drawn into the specimen entrance with a rate of 1.5 ml/min by the pump, in order to make the circulating tumor cell be captured by the porous membrane with the pore diameter of 8 micrometer. Then, the channel chip is detached from the chip system and a testing drug is added on the channel chip. Then, the first layer cover is stacked and the testing drug is added into the first layer cover. Then, the second layer cover is stacked and the assembly is put in a 3.5 mm petri dish. Then, the petri dish is put in an incubator with an environment of 5% $CO_2$ and 37° C. for culturing 24 hours. After the culture is complete, excess medium is drawn out by lens wipes, and an analysis reagent is added for observation.

Figure 21:
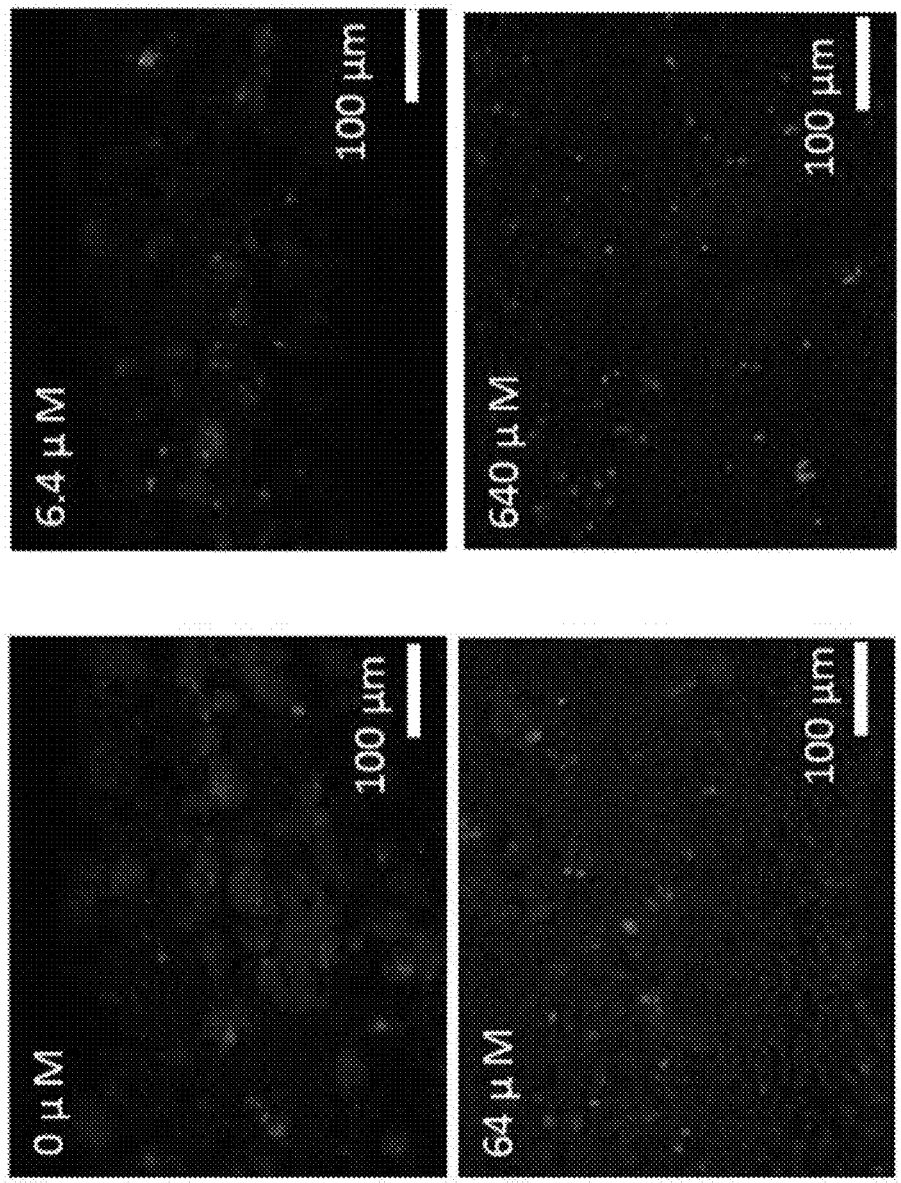
FIG. 21 is a result image of drug sensitivity analysis $IC_{50}$.
Figure 22:
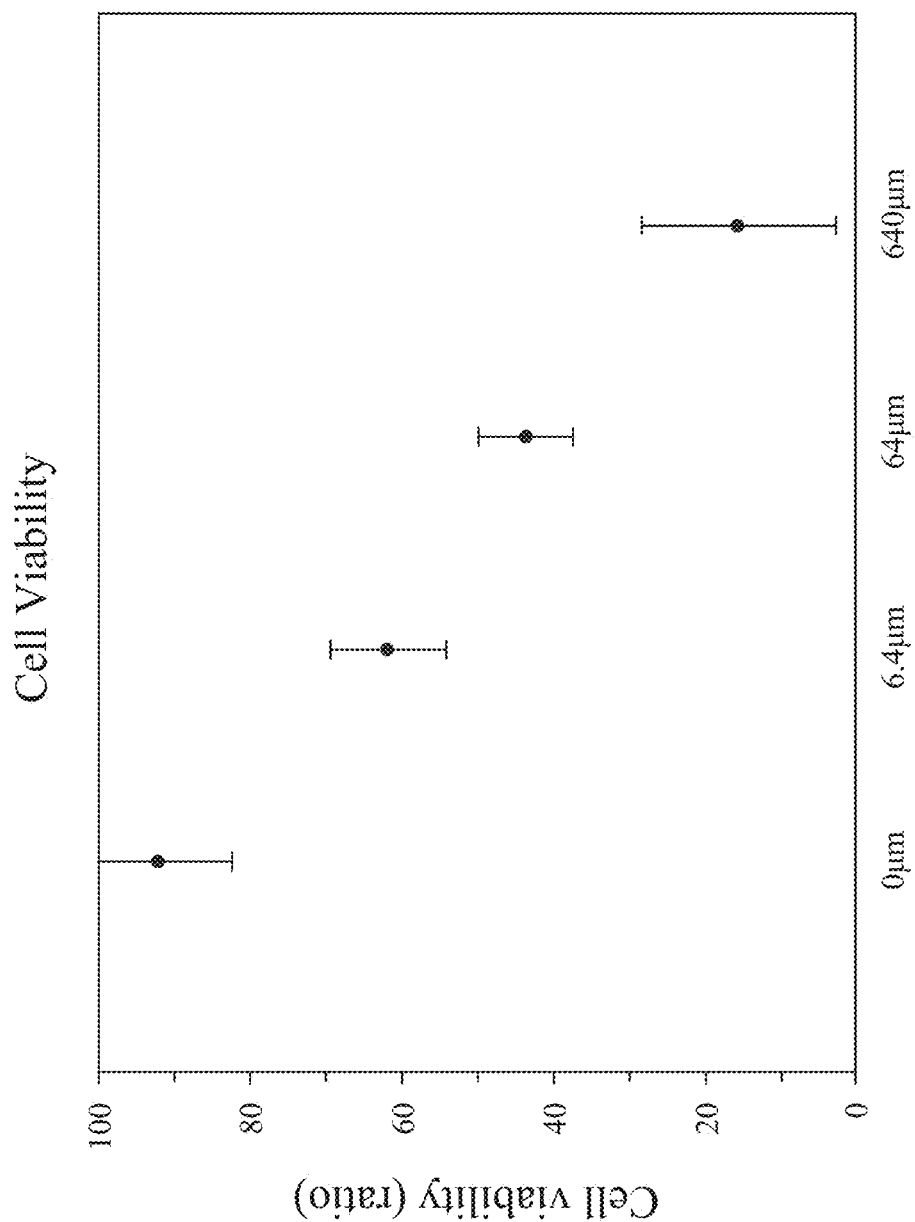
FIG. 22 is a result graph showing drug concentrations to cell viabilities.

Please refer to FIG. 21 and FIG. 22. FIG. 21 is a result image of drug sensitivity analysis $IC_{50}$. FIG. 22 is a result graph showing drug concentrations to cell viabilities. In FIG. 21 and FIG. 22, the cell viability decreases as the drug concentration increases. In this regard, a relationship graph of concentration to viability is predictable and obtained, in order to infer a real $IC_{50}$ range, which doctors can base on to determine the drug sensitivity.

Efficiency of Capturing Different Testing Cancer Cells

The testing cancer cells used in following experiments are A549 cells and CL1-5 cells. The specimen used includes 5 ml medium and $3\times10^4$ A549 cells or $3\times10^4$ CL1-5 cells.

The experimental steps are as follows: first, a buffer solution is pumped into the specimen exit by the pump, in order to evacuate the air in the chip system. Then, the specimen is drawn into the specimen entrance with a rate of 1.5 ml/min by the pump, in order to make the circulating tumor cell be captured by the porous membrane with the pore diameter of 8 micrometer. Then, a buffer solution is pumped into the specimen exit with a rate of 5 ml/min by the pump, and a separated solution is collected at the specimen entrance. Finally, the separated solution is centrifuged at 1200×g of rotor speed and room temperature for 20 minutes, and drawn out for microscopy observation.

Figure 23B:
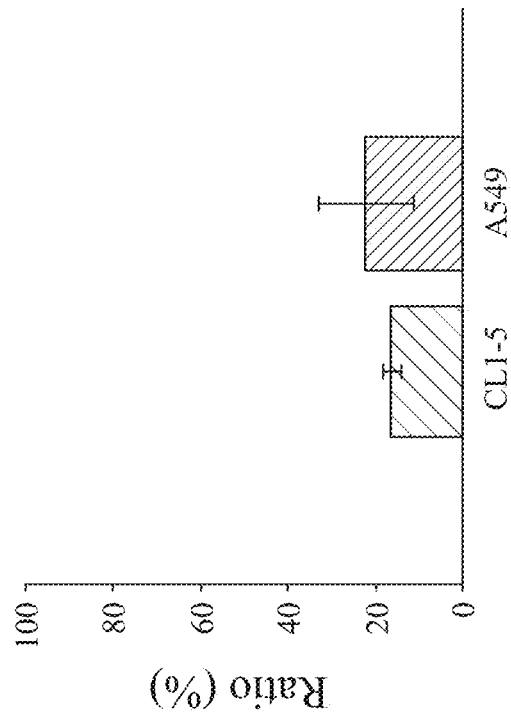
FIG. 23B is a result graph showing the ratios of different kinds of testing cancer cells being captured.
Figure 23A:
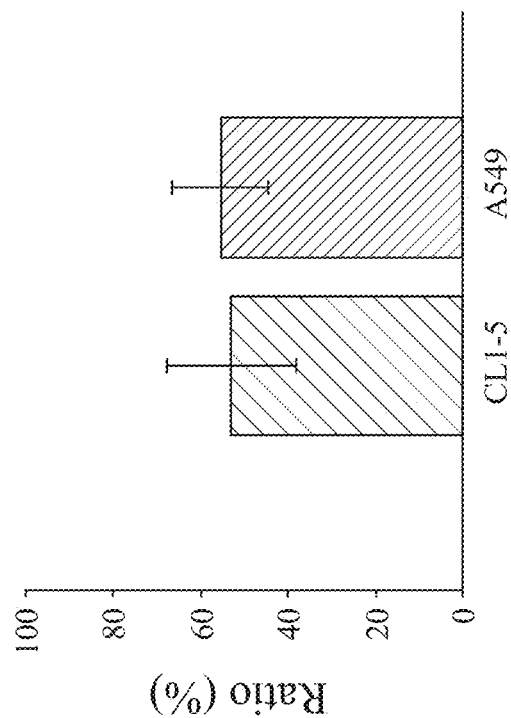
FIG. 23A is a result graph showing the ratios of different kinds of testing cancer cells passing through the porous membrane.

Please refer to FIG. 23A and FIG. 23B. FIG. 23A is a result graph showing the ratios of different kinds of testing cancer cells passing through the porous membrane. FIG. 23B is a result graph showing the ratios of different kinds of testing cancer cells being captured. In FIG. 23A and FIG. 23B, even replace the A549 cells with the CL1-5 cells, the ratios of cells passing through the porous membrane and the ratios of cells being captured remain almost the same.

In summary, based on the different physical properties of cell sizes, the present disclosure provides the circulating tumor cell capture device and the method for circulating tumor cell capture with simple manufacturing process, easy operation and quick analysis. The device and method use the porous membrane to separate blood cells and cancer cells, so as to make the low ratio of cancer cells in the specimen be captured by the chip system. The captured cancer cells are washed out and identified as living cells, which can be further cultured into a large-scale or establish a cell line. In addition, the present disclosure also provides a method for circulating tumor cell capture and drug sensitivity analysis, which is for each of the cancer cells to be analyzed in situ on the circulating tumor cell capture device to directly verify cell identity or test the drug sensitivity through drug effect analysis. The examples of the present disclosure prove that the circulating tumor cell capture device and the method thereof are capable of effectively separating cancer cells, and being a device platform for rapid in situ analysis and screening.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A circulating tumor cell capture device configured to capture a circulating tumor cell in a specimen, comprising:
   a chip system, comprising:
      a confluence chip, comprising an upper surface and a lower surface, wherein the upper surface comprises a specimen entrance, a specimen exit, a specimen entering channel and a specimen exiting channel, and wherein the specimen entrance communicates with the specimen entering channel, and the specimen exit communicates with the specimen exiting channel;
      a lower chip set disposed at the lower surface of the confluence chip, comprising:
         a channel chip disposed at the lower surface of the confluence chip, comprising:
            a channel chip upper layer comprising one fluid access communicating with the specimen entering channel of the confluence chip, and an upper channel pattern structure; and
            a channel chip lower layer stacked below the channel chip upper layer, wherein the channel chip lower layer comprises another fluid access communicating with the fluid access of the channel chip upper layer, and a lower channel pattern structure corresponding to the upper channel pattern structure;
         a split chip detachably stacked below the channel chip, wherein the split chip comprises a split pattern channel configured to make the specimen split evenly; and
         a porous membrane disposed between the upper channel pattern structure and the lower channel pattern structure, wherein the specimen is capable of passing through the porous membrane and flowing between the channel chip and the split chip to make the circulating tumor cell be captured by the porous membrane; and
      a pump pipe-connected to the specimen exit and the specimen entrance of the confluence chip to make the specimen circularly flow in the chip system.

2. The circulating tumor cell capture device of claim 1, wherein a pore diameter of the porous membrane is 5-12 micrometer.

3. The circulating tumor cell capture device of claim 1, wherein a number of the upper channel pattern structure and the lower channel pattern structure is 4, respectively.

4. The circulating tumor cell capture device of claim 1, wherein the split pattern channel of the split chip is an H-shaped channel.

5. A method for circulating tumor cell capture, comprising:
   providing a specimen;
   providing the circulating tumor cell capture device of claim 1;
   performing a specimen pretreating step configured to reduce an amount of blood cells in the specimen, in order to obtain a separated specimen with the circulating tumor cell; and
   performing a capturing step configured to draw the separated specimen into the specimen entrance, and make the separated specimen flow between the channel chip and the split chip and pass through the porous membrane by the pump, in order to make the circulating tumor cell be captured by the porous membrane.

6. The method for circulating tumor cell capture of claim 5, further comprising a negative pressure system establishing step after the specimen pretreating step, wherein the negative pressure system establishing step comprises pumping a buffer solution into the specimen exit by the pump, in order to evacuate the air in the chip system.

7. The method for circulating tumor cell capture of claim 5, further comprising a washing out step after the capturing step, wherein the washing out step comprises pumping a buffer solution into the specimen exit by the pump, and collecting a separated solution at the specimen entrance.

8. The method for circulating tumor cell capture of claim 7, further comprising a centrifuging step after the washing out step, wherein the centrifuging step comprises centrifuging the separated solution to obtain the isolated circulating tumor cell.

9. The method for circulating tumor cell capture of claim 7, wherein a wash-out rate of the pump is 0.5 ml/min to 10 ml/min in the washing out step.

10. A method for circulating tumor cell capture and drug sensitivity analysis, comprising:
    providing a specimen;
    providing the circulating tumor cell capture device of claim 3;

performing a specimen pretreating step configured to reduce an amount of blood cells in the specimen, in order to obtain a separated specimen with the circulating tumor cell;

performing a capturing step configured to draw the separated specimen into the specimen entrance, and make the separated specimen flow between the channel chip and the split chip and pass through the porous membrane by the pump, in order to make the circulating tumor cell be captured by the porous membrane;

performing a detaching step configured to detach the lower chip set from the chip system;

performing a drug adding step configured to detach the channel chip from the lower chip set, and to add at least one testing drug on the channel chip;

performing a culturing step configured to culture the channel chip with the at least one testing drug added under a culture condition for a culture time; and performing a drug sensitivity analysis result determining step.

11. The method for circulating tumor cell capture and drug sensitivity analysis of claim 10, further comprising a negative pressure system establishing step after the specimen pretreating step, wherein the negative pressure system establishing step comprises pumping a buffer solution into the specimen exit by the pump, in order to evacuate the air in the chip system.

12. The method for circulating tumor cell capture and drug sensitivity analysis of claim 10, after the drug adding step, further comprising:

performing a wetting step configured to stack a first layer cover on the channel chip, and to draw the at least one testing drug into the first layer cover; and performing a covering step configured to stack a second layer cover on the first layer cover.

13. The method for circulating tumor cell capture and drug sensitivity analysis of claim 10, wherein a draw-in rate of the pump making the separated specimen flow between the channel chip and the split chip is 0.5 ml/min to 10 ml/min in the capturing step.

14. The method for circulating tumor cell capture and drug sensitivity analysis of claim 10, wherein the drug sensitivity analysis result determining step comprises:

adding an analysis reagent to the channel chip; and performing an analyzing step to determine whether the circulating tumor cell is resistant to the at least one testing drug or not.

15. The method for circulating tumor cell capture and drug sensitivity analysis of claim 10, wherein the drug sensitivity analysis result determining step comprises:

determining a minimal concentration range of the circulating tumor cell being resistant to the at least one testing drug.

* * * * *